United States Patent
Bullington et al.

(10) Patent No.: US 9,999,383 B2
(45) Date of Patent: *Jun. 19, 2018

(54) SYRINGE-BASED FLUID DIVERSION MECHANISM FOR BODILY FLUID SAMPLING

(71) Applicant: Magnolia Medical Technologies, Inc., Seattle, WA (US)

(72) Inventors: Gregory J. Bullington, Bellevue, WA (US); Richard G. Patton, Seattle, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/264,481

(22) Filed: Apr. 29, 2014

(65) Prior Publication Data
US 2015/0073348 A1 Mar. 12, 2015

Related U.S. Application Data

(63) Continuation of application No. PCT/US2013/072563, filed on Dec. 2, 2013.
(Continued)

(51) Int. Cl.
*A61B 5/15* (2006.01)
*A61B 5/153* (2006.01)
(Continued)

(52) U.S. Cl.
CPC ...... *A61B 5/150251* (2013.01); *A61B 5/1405* (2013.01); *A61B 5/1416* (2013.01);
(Continued)

(58) Field of Classification Search
CPC . A61B 5/150251; A61B 5/153; A61B 5/1405; A61B 10/0045; A61B 5/1416;
(Continued)

(56) References Cited

U.S. PATENT DOCUMENTS 2,707,953 A 5/1955 Ryan
2,992,974 A 7/1961 Belcove et al.
(Continued)

FOREIGN PATENT DOCUMENTS

EP 0761173 3/1997
EP 0608985 4/1997
(Continued)

OTHER PUBLICATIONS

Office Action for U.S. Appl. No. 14/089,267, dated Jun. 19, 2014, 13 pages.
(Continued)

*Primary Examiner* — Bhisma Mehta
*Assistant Examiner* — Brandy S Lee
(74) *Attorney, Agent, or Firm* — Cooley LLP

(57) ABSTRACT

A syringe-based device includes a housing, a pre-sample reservoir, and an actuator. The housing defines an inner volume between a substantially open proximal end portion and a distal end portion that includes a port couplable to a lumen-defining device. The pre-sample reservoir is fluidically couplable to the port to receive and isolate a first volume of bodily fluid. The actuator is at least partially disposed in the inner volume and has a proximal end portion that includes an engagement portion and a distal end portion that includes a sealing member. The engagement portion is configured to allow a user to selectively move the actuator between a first configuration such that bodily fluid can flow from the port to the pre-sample reservoir, and a second configuration such that bodily fluid can flow from the port to a sample reservoir defined at least in part by the sealing member and the housing.

30 Claims, 22 Drawing Sheets

Related U.S. Application Data

(60) Provisional application No. 61/731,620, filed on Nov. 30, 2012.

(51) Int. Cl.
*A61B 10/00* (2006.01)
*A61B 5/155* (2006.01)
*A61B 5/154* (2006.01)

(52) U.S. Cl.
CPC .......... *A61B 5/1427* (2013.01); *A61B 5/1438* (2013.01); *A61B 5/153* (2013.01); *A61B 5/15003* (2013.01); *A61B 5/154* (2013.01); *A61B 5/155* (2013.01); *A61B 5/150221* (2013.01); *A61B 5/150236* (2013.01); *A61B 5/150244* (2013.01); *A61B 5/150343* (2013.01); *A61B 5/150389* (2013.01); *A61B 5/150633* (2013.01); *A61B 10/0045* (2013.01); *A61B 5/150732* (2013.01)

(58) Field of Classification Search
CPC ..... A61B 5/1427; A61B 5/1438; A61B 5/154; A61B 5/15003; A61B 5/150221; A61B 5/150236; A61B 5/150244; A61B 5/150343; A61B 5/150389; A61B 5/150633; A61M 2005/3128; A61M 5/31501; A61M 2005/1787; A61M 2005/31598; A61M 5/31596
USPC .................................................. 604/187, 191
See application file for complete search history.

(56) References Cited

U.S. PATENT DOCUMENTS

| | | | |
|---|---|---|---|
| 3,013,557 | A | 12/1961 | Pallotta |
| 3,098,016 | A | 7/1963 | Cooper et al. |
| 3,382,865 | A | 5/1968 | Worral, Jr. |
| 3,405,706 | A | 10/1968 | Cinqualbre |
| 3,494,351 | A | 2/1970 | Horn |
| 3,577,980 | A | 5/1971 | Cohen |
| 3,635,798 | A | 1/1972 | Kirkham et al. |
| 3,648,684 | A | 3/1972 | Barnwell et al. |
| 3,680,558 | A | 8/1972 | Kapelowitz |
| 3,777,773 | A | 12/1973 | Tolbert |
| 3,831,602 | A * | 8/1974 | Broadwin ............... 604/210 |
| 3,848,579 | A | 11/1974 | Villa-Real |
| 3,848,581 | A | 11/1974 | Cinqualbre et al. |
| 3,890,203 | A | 6/1975 | Mehl |
| 3,890,968 | A | 6/1975 | Pierce et al. |
| 3,937,211 | A | 2/1976 | Merten |
| 3,960,139 | A * | 6/1976 | Bailey ............... A61B 5/1416 |
| | | | 600/575 |
| 4,057,050 | A | 11/1977 | Sarstedt |
| 4,063,460 | A | 12/1977 | Svensson |
| 4,133,863 | A | 1/1979 | Koenig |
| 4,166,450 | A | 9/1979 | Abramson |
| 4,210,173 | A | 7/1980 | Choksi et al. |
| 4,212,308 | A | 7/1980 | Percarpio |
| 4,340,067 | A | 7/1982 | Rattenborg |
| 4,370,987 | A | 2/1983 | Bazell et al. |
| 4,411,275 | A | 10/1983 | Raitto |
| 4,425,235 | A | 1/1984 | Cornell et al. |
| 4,444,203 | A | 4/1984 | Engelman |
| 4,459,997 | A | 7/1984 | Sarstedt |
| 4,509,534 | A | 4/1985 | Tassin, Jr. |
| 4,537,593 | A | 8/1985 | Alchas |
| 4,657,160 | A | 4/1987 | Woods et al. |
| 4,673,386 | A | 6/1987 | Gordon |
| 4,676,256 | A | 6/1987 | Golden |
| 4,715,854 | A * | 12/1987 | Vaillancourt ............... 604/191 |
| 4,737,146 | A | 4/1988 | Amaki et al. |
| 4,790,830 | A | 12/1988 | Hamacher |
| 4,808,157 | A | 2/1989 | Coombs |
| 4,820,287 | A | 4/1989 | Leonard |
| 4,865,583 | A | 9/1989 | Tu |
| 4,890,627 | A | 1/1990 | Haber et al. |
| 4,988,339 | A | 1/1991 | Vadher |
| 5,009,847 | A | 4/1991 | Solomons |
| 5,097,842 | A | 3/1992 | Bonn |
| 5,100,390 | A | 3/1992 | Lubeck et al. |
| 5,108,927 | A | 4/1992 | Dom |
| 5,122,129 | A | 6/1992 | Olson et al. |
| 5,234,406 | A | 8/1993 | Drasner et al. |
| 5,269,317 | A | 12/1993 | Bennett |
| 5,330,464 | A | 7/1994 | Mathias et al. |
| 5,360,011 | A | 11/1994 | McCallister |
| 5,395,339 | A * | 3/1995 | Talonn ............... A61M 5/31511 |
| | | | 604/110 |
| 5,429,610 | A * | 7/1995 | Vaillancourt ............... 604/191 |
| 5,449,351 | A | 9/1995 | Zohmann |
| 5,450,856 | A | 9/1995 | Norris |
| 5,454,786 | A | 10/1995 | Harris |
| 5,485,854 | A | 1/1996 | Hollister |
| 5,507,299 | A | 4/1996 | Roland |
| 5,522,804 | A * | 6/1996 | Lynn ............... A61M 5/002 |
| | | | 604/187 |
| 5,573,510 | A | 11/1996 | Isaacson |
| 5,577,513 | A | 11/1996 | Van Vlassalaer |
| 5,603,700 | A | 2/1997 | Daneshvar |
| 5,628,734 | A | 5/1997 | Hatfalvi |
| 5,649,912 | A | 7/1997 | Peterson |
| 5,718,678 | A | 2/1998 | Fleming, III |
| 5,762,633 | A | 6/1998 | Whisson |
| 5,785,682 | A * | 7/1998 | Grabenkort ............... A61M 5/284 |
| | | | 604/191 |
| 5,848,996 | A | 12/1998 | Eldor |
| 5,865,812 | A | 2/1999 | Correia |
| 5,882,318 | A | 3/1999 | Boyde |
| 5,922,551 | A | 7/1999 | Durbin et al. |
| 5,971,956 | A | 10/1999 | Epstein |
| 6,016,712 | A | 1/2000 | Warden et al. |
| 6,057,105 | A | 5/2000 | Hoon et al. |
| 6,126,643 | A * | 10/2000 | Vaillancouert ............... A61B 5/15003 |
| | | | 600/576 |
| 6,159,164 | A | 12/2000 | Neese et al. |
| 6,210,909 | B1 | 4/2001 | Guirguis |
| 6,299,131 | B1 | 10/2001 | Ryan |
| 6,328,726 | B1 | 12/2001 | Ishida et al. |
| 6,364,890 | B1 | 4/2002 | Lum et al. |
| 6,368,306 | B1 * | 4/2002 | Koska ............... A61M 5/5066 |
| | | | 604/218 |
| 6,387,086 | B2 | 5/2002 | Mathias et al. |
| 6,403,381 | B1 | 6/2002 | Mann et al. |
| 6,520,948 | B1 | 2/2003 | Mathias et al. |
| 6,592,555 | B1 * | 7/2003 | Wen-Pi ............... A61M 5/322 |
| | | | 128/919 |
| 6,626,884 | B1 | 9/2003 | Dillon et al. |
| 6,692,479 | B2 | 2/2004 | Kraus et al. |
| 6,716,187 | B1 | 4/2004 | Jorgensen et al. |
| 6,746,420 | B1 | 6/2004 | Prestidge et al. |
| 6,913,580 | B2 | 7/2005 | Stone |
| 7,025,751 | B2 | 4/2006 | Silva et al. |
| 7,044,941 | B2 | 5/2006 | Mathias et al. |
| 7,087,047 | B2 | 8/2006 | Kraus et al. |
| 7,204,828 | B2 | 4/2007 | Rosiello |
| 7,335,188 | B2 | 2/2008 | Graf |
| 7,384,416 | B2 | 6/2008 | Goudaliez et al. |
| 7,744,573 | B2 | 6/2010 | Gordon et al. |
| 7,993,310 | B2 | 8/2011 | Rosiello |
| 8,197,420 | B2 | 6/2012 | Patton |
| 8,231,546 | B2 | 7/2012 | Patton |
| 8,292,841 | B2 | 10/2012 | Gregersen |
| 8,337,418 | B2 | 12/2012 | Patton |
| 8,535,241 | B2 | 9/2013 | Bullington et al. |
| 8,647,286 | B2 | 2/2014 | Patton |
| 8,864,684 | B2 | 10/2014 | Bullington et al. |
| 8,876,734 | B2 | 11/2014 | Patton |
| 9,022,950 | B2 | 5/2015 | Bullington et al. |
| 9,022,951 | B2 | 5/2015 | Bullington et al. |
| 9,060,724 | B2 | 6/2015 | Bullington et al. |
| 9,060,725 | B2 | 6/2015 | Bullington et al. |
| 9,149,576 | B2 | 10/2015 | Bullington et al. |

(56) References Cited

U.S. PATENT DOCUMENTS

| | | | |
|---|---|---|---|
| 9,155,495 B2 | 10/2015 | Bullington et al. | |
| 9,204,864 B2 | 12/2015 | Bullington et al. | |
| 2002/0002349 A1 | 1/2002 | Flaherty et al. | |
| 2002/0107469 A1 | 8/2002 | Bolan et al. | |
| 2002/0183651 A1 | 12/2002 | Hyun | |
| 2002/0193751 A1 | 12/2002 | Theeuwes et al. | |
| 2003/0055381 A1 | 3/2003 | Wilkinson | |
| 2003/0069543 A1 | 4/2003 | Carpenter et al. | |
| 2003/0208151 A1 | 11/2003 | Kraus et al. | |
| 2004/0009542 A1 | 1/2004 | Dumont et al. | |
| 2004/0010228 A1 | 1/2004 | Swenson et al. | |
| 2004/0054283 A1 | 3/2004 | Corey et al. | |
| 2004/0054333 A1 | 3/2004 | Theeuwes et al. | |
| 2004/0147855 A1 | 7/2004 | Marsden | |
| 2005/0004524 A1 | 1/2005 | Newby et al. | |
| 2005/0148993 A1 | 7/2005 | Mathias et al. | |
| 2005/0154368 A1 | 7/2005 | Lim et al. | |
| 2005/0240161 A1 | 10/2005 | Crawford | |
| 2005/0245885 A1 | 11/2005 | Brown | |
| 2005/0281713 A1 | 12/2005 | Hampsch et al. | |
| 2006/0287639 A1 | 12/2006 | Sharp | |
| 2007/0100250 A1 | 5/2007 | Kline | |
| 2007/0119508 A1 | 5/2007 | West et al. | |
| 2007/0287948 A1 | 12/2007 | Sakiewicz | |
| 2008/0108954 A1 | 5/2008 | Mathias et al. | |
| 2008/0145933 A1 | 6/2008 | Patton | |
| 2008/0255523 A1* | 10/2008 | Grinberg | A61M 5/008 604/192 |
| 2009/0306601 A1 | 12/2009 | Shaw et al. | |
| 2010/0152681 A1 | 6/2010 | Mathias | |
| 2010/0286513 A1 | 11/2010 | Pollard et al. | |
| 2012/0035540 A1 | 2/2012 | Ferren et al. | |
| 2012/0095367 A1 | 4/2012 | Patton | |
| 2012/0215131 A1 | 8/2012 | Patton | |
| 2013/0079604 A1 | 3/2013 | Patton | |
| 2013/0116599 A1 | 5/2013 | Bullington et al. | |
| 2013/0317391 A1 | 11/2013 | Bullington et al. | |
| 2014/0039348 A1 | 2/2014 | Bullington et al. | |
| 2014/0081172 A1 | 3/2014 | Patton | |
| 2014/0107564 A1 | 4/2014 | Bullington et al. | |
| 2014/0124542 A1 | 5/2014 | Kojima et al. | |
| 2014/0155781 A1 | 6/2014 | Bullington et al. | |
| 2014/0155782 A1 | 6/2014 | Bullington et al. | |
| 2014/0163419 A1 | 6/2014 | Bullington et al. | |
| 2015/0018715 A1 | 1/2015 | Walterspiel | |
| 2015/0094615 A1 | 4/2015 | Patton | |
| 2015/0257691 A1 | 9/2015 | Bullington et al. | |
| 2015/0342510 A1 | 12/2015 | Bullington et al. | |
| 2016/0361006 A1 | 12/2016 | Bullington et al. | |

FOREIGN PATENT DOCUMENTS

| | | |
|---|---|---|
| EP | 0727187 | 8/2003 |
| WO | WO 1997/018845 | 5/1997 |
| WO | WO 2000/041624 | 7/2000 |
| WO | WO 2005/068011 | 7/2005 |
| WO | WO 2008/077047 | 6/2008 |
| WO | WO 2013/181352 | 12/2013 |
| WO | WO 2014/022275 | 2/2014 |
| WO | WO 2014/022750 | 2/2014 |
| WO | WO 2014/058945 | 4/2014 |
| WO | WO 2014/085800 | 6/2014 |
| WO | WO 2014/089186 | 6/2014 |
| WO | WO 2014/099266 | 6/2014 |

OTHER PUBLICATIONS

International Search Report and Written Opinion for International Application No. PCT/US2013/071491, dated Aug. 5, 2014, 9 pages.
Office Action for U.S. Appl. No. 14/493,796, dated Jan. 27, 2015, 7 pages.
Office Action for U.S. Appl. No. 14/494,208, dated Jan. 27, 2015, 7 pages.
International Search Report and Written Opinion for International Application No. PCT/US2013/073080, dated Feb. 18, 2014, 14 pages.
International Search Report and Written Opinion for International Application No. PCT/US2013/063975, dated Mar. 20, 2014, 16 pages.
Office Action for U.S. Appl. No. 14/049,326, dated Apr. 24, 2015, 10 pages.
International Search Report and Written Opinion for International Application No. PCT/US2013/052493, dated Nov. 27, 2013, 7 pages.
Office Action for U.S. Appl. No. 13/952,964, dated Mar. 20, 2015, 11 pages.
Medical Surgical Systems Catalogue (Canadian Version), BD Medical, 2010, 51 pages.
Order of Draw for Multiple Tube Collections, LabNotes, a newsletter from BD Diagnostics,—Preanalytical Systems, vol. 17, No. 1, 2007.
Calam, Roger R., Recommended "Order of Draw" for Collecting Blood Specimens Into Additive-Containing Tubes, Letter to the Editor, Clinical Chemistry, vol. 28, No. 6, 1982.
Arkin, Charles F., et al., "Procedures for the Collection of Diagnostic Blood Specimens by Venipuncture; Approved Standard," Fifth Edition, NCCLS, vol. 23, No. 32, 2003.
Patton, Richard G., et al., "Innovation for Reducing Blood Culture Contamination: Initial Specimen Diversion Technique," Journal of Clinical MicroBiology, Dec. 2010, p. 4501-4503.
Wang, P., et al., "Strategies on reducing blood culture contamination," Wolters Kluwer Health I Lippincott Williams & Wilkins, 2012.
Kim, J., et al., "The Sum of the Parts is Greater Than the Whole: Reducing Blood Culture Contamination," Annals of Internal Medicine, American College of Physicians, 2011.
Stohl, S., et al., Blood Cultures at Central Line Insertion in the Intensive Care Unit: Comparison with Peripheral Venipuncture, Journal of Clinical Microbiology, Jul. 2011, p. 2398-2403.
Sibley, C., et al., "Molecular methods for pathogen and microbial community detection and characterization: Current and potential application in diagnostic microbiology," Infection, Genetics and Evolution 12, 2012.
Levin, P., et al., "Use of the Nonwire Central Line Hub to Reduce Blood Culture Contamination," Chest, 2013.
Schuur, J., "Blood Cultures: When Do they Help and When Do They Harm?" Clinical Decision Making in Emergency Medicine, Mount Sinai, Jun. 2012.
Proehl, J., et al., "Clinical Practice Guideline: Prevention of Blood Culture Contamination," Emergency Nurses Association, Dec. 2012.
Hall, K., et al., "Updated Review of Blood Culture Contamination," Clinical Microbiology Reviews, Oct. 2006, p. 788-802.
International Search Report and Written Opinion dated May 16, 2008, which issued during the prosecution of International Patent Application No. PCT/US2007/087951 (8 pages).
Wagner et al. "Diversion of Initial Blood Flow to Prevent Whole-Blood Contamination by Skin Surface Bacteria: an in vitro model," Transfusion, vol. 40, Mar. 2000, pp. 335-338I.
Office Action for U.S. Appl. No. 11/955,635, dated Jul. 22, 2010, 11 pages.
Office Action for U.S. Appl. No. 11/955,635, dated Dec. 3, 2010, 11 pages.
Office Action for U.S. Appl. No. 13/335,241, dated Apr. 20, 2012, 12 pages.
Office Action for U.S. Appl. No. 13/458,508, dated Jul. 24, 2012, 13 pages.
International Search Report and Written Opinion dated Oct. 24, 2013, issued for International Patent Application No. PCT/US2013/043289 (15 pages).
Office Action for U.S. Appl. No. 13/675,295, dated May 23, 2013, 15 pages.
Office Action for U.S. Appl. No. 13/954,528, dated Mar. 17, 2014, 10 pages.

(56) References Cited

OTHER PUBLICATIONS

International Search Report and Written Opinion dated Feb. 7, 2014, which issued during the prosecution of International Patent Application No. PCT/US2013/072563 (11 pages).
Supplementary European Search Report for European Application No. 13797732.8, dated Dec. 7, 2015, 6 pages.
Office Action for Chinese Application No. 201380071681.4, dated Aug. 16, 2016, 9 pages.
Extended European Search Report for European Application No. 13859067.4, dated Jun. 7, 2016, 4 pages.
Notification of the First Office Action for Chinese Application No. 201380072185.0, dated Sep. 28, 2016, 9 pages.
International Search Report and Written Opinion for International Application No. PCT/US2016/037160, dated Sep. 30, 2016, 10 pages.
Extended European Search Report for European Application No. 13859067.4, dated Jan. 27, 2017, 4 pages.
Office Action for U.S. Appl. No. 15/432,310, dated Apr. 12, 2017, 23 pages.
Office Action for U.S. Appl. No. 15/435,684, dated Jun. 12, 2017, 28 pages.
Office Action for U.S. Appl. No. 15/457,082, dated Jun. 15, 2017, 22 pages.
Office Action for U.S. Appl. No. 15/448,891, dated Jun. 16, 2017, 34 pages.

\* cited by examiner

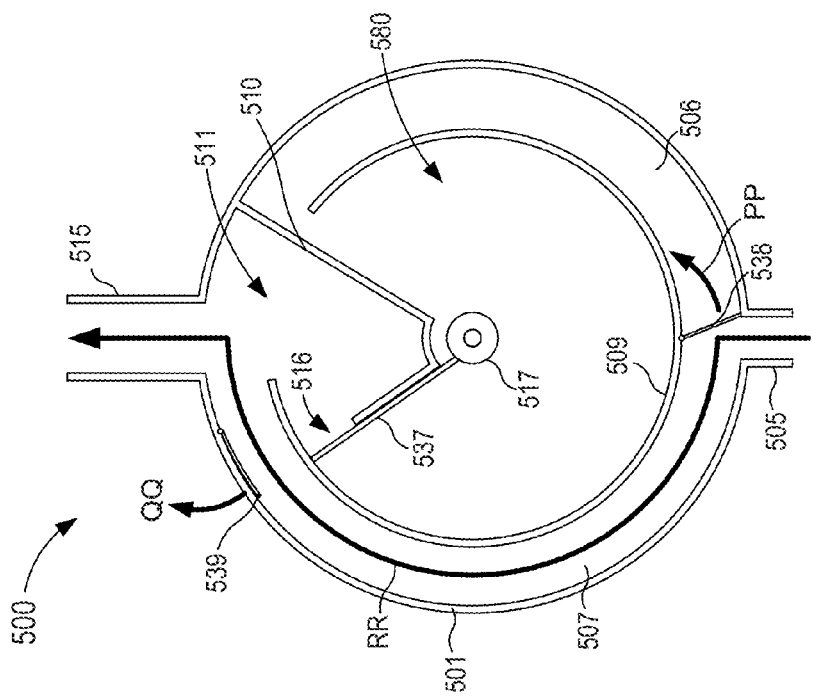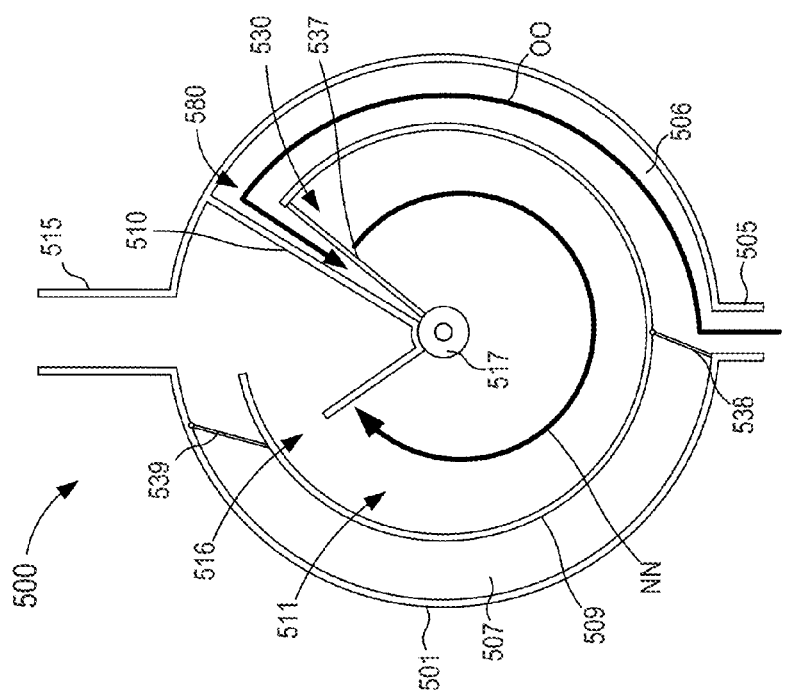

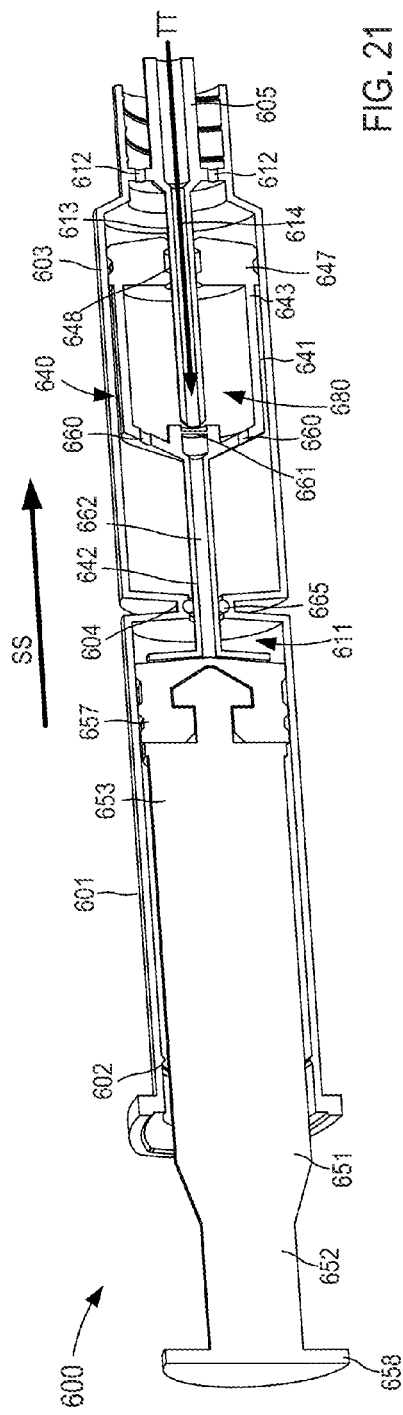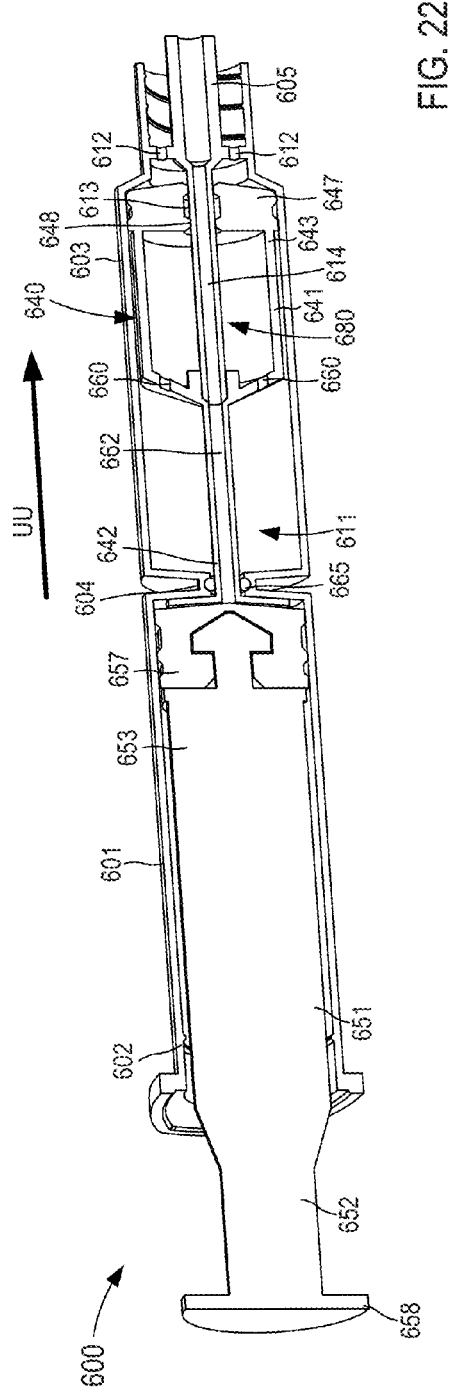

SYRINGE-BASED FLUID DIVERSION MECHANISM FOR BODILY FLUID SAMPLING

CROSS-REFERENCE TO RELATED APPLICATIONS

This application is a continuation of International Patent Application No. PCT/US2013/072563, filed Dec. 2, 2013, entitled "Syringe-Based Fluid Diversion Mechanism for Bodily Fluid Sampling," which claims priority to and the benefit of U.S. Provisional Application Ser. No. 61/731,620, filed Nov. 30, 2012, entitled "Syringe-Based Fluid Diversion Mechanism for Bodily Fluid Sampling," the disclosures of which are incorporated herein by reference in their entirety.

BACKGROUND

Embodiments described herein relate generally to the parenteral procurement of bodily-fluid samples, and more particularly to devices and methods for parenterally-procuring bodily-fluid samples with reduced contamination from microbes or other contaminants exterior to the bodily-fluid source, such as dermally-residing microbes.

Health care practitioners routinely perform various types of microbial tests on patients using parenterally-obtained bodily-fluids. In some instances, patient samples (e.g., bodily-fluids) are tested for the presence of one or more potentially undesirable microbes, such as bacteria, fungi, or yeast (e.g., Candida). Microbial testing may include incubating patient samples in one or more sterile vessels containing culture media that is conducive to microbial growth, real-time diagnostics, and/or PCR-based approaches. Generally, when such microbes are present in the patient sample, the microbes flourish over time in the culture medium. After a pre-determined amount of time (e.g., a few hours to several days), the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

Patient samples, however, can become contaminated during procurement. One way in which contamination of a patient sample may occur is by the transfer of microbes from a bodily surface (e.g., dermally-residing microbes) dislodged during needle insertion into a patient and subsequently transferred to a culture medium with the patient sample. The bodily surface and/or other undesirable external microbes may be dislodged either directly or via dislodged tissue fragments, hair follicles, sweat glands and other adnexal structures. Another possible source of contamination is from the person drawing the patient sample. For example, a doctor, phlebotomist, nurse, etc. can transfer contaminants from their body (e.g., finger, arms, etc.) to the patient sample. The transferred microbes may thrive in the culture medium and eventually yield a positive microbial test result, thereby falsely indicating the presence of such microbes in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the health care system.

As such, a need exists for improved bodily-fluid transfer devices and methods that reduce microbial contamination in bodily-fluid test samples.

SUMMARY

Devices for parenterally-procuring bodily-fluid samples with reduced contamination from microbes exterior to the bodily-fluid source, such as dermally-residing microbes, are described herein. In some embodiments, a syringe-based device for parenterally-procuring bodily fluid samples with reduced contamination from a patient includes a housing, a pre-sample reservoir, and an actuator mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The pre-sample reservoir is fluidically couplable to the port and is configured to receive and isolate a first volume of bodily fluid withdrawn from the patient. The actuator mechanism is at least partially disposed in the inner volume of the housing and has a proximal end portion and a distal end portion. The distal end portion includes a sealing member and the proximal end portion includes an engagement portion configured to allow a user to selectively move the actuator mechanism between a first configuration in which the bodily fluid can flow from the port to the pre-sample reservoir, and a second configuration in which the bodily fluid can flow from the port to a sample reservoir defined at least in part by the sealing member and the housing.

BRIEF DESCRIPTION OF THE DRAWINGS

FIGS. 16 and 17 are schematic illustrations of at least a portion of a syringe-based transfer device in a first configuration and a second configuration, respectively, according to an embodiment.

FIG. 21 is a cross-sectional view of the syringe-based transfer device of FIG. 18 taken along the line $X_4$-$X_4$, in a second configuration.

FIG. 22 is a cross-sectional view of the syringe-based transfer device of FIG. 18 taken along the line $X_4$-$X_4$, in a third configuration.

DETAILED DESCRIPTION

Figure 1:
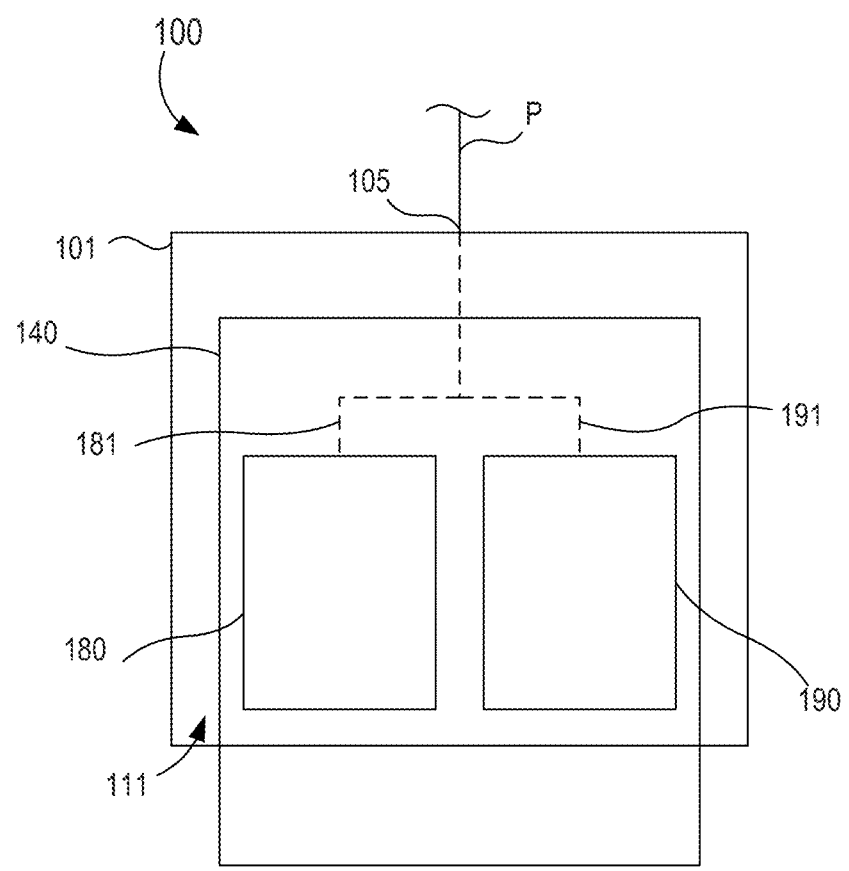
FIG. 1 is a schematic illustration of a syringe-based transfer device according to an embodiment.

Devices for parenterally-procuring bodily-fluid samples with reduced contamination from microbes exterior to the bodily-fluid source, such as dermally-residing microbes, are described herein. In some embodiments, a syringe-based device for parenterally-procuring bodily fluid samples with reduced contamination from a patient includes a housing, a pre-sample reservoir, and an actuator mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The pre-sample reservoir is fluidically couplable to the port and is configured to receive and isolate a first volume of bodily fluid withdrawn from the patient. The actuator mechanism is at least partially disposed in the inner volume of the housing and has a proximal end portion and a distal end portion. The distal end portion includes a sealing member and the proximal end portion includes an engagement portion configured to allow a user to selectively move the actuator mechanism between a first configuration in which the bodily fluid can flow from the port to the pre-sample reservoir, and a second configuration in which the bodily fluid can flow from the port to a sample reservoir defined at least in part by the sealing member and the housing.

In some embodiments, a syringe-based device for parenterally-procuring bodily fluid samples with reduced contamination from a patient includes a housing and an actuator mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The actuator mechanism is movably disposed in the inner volume. The actuator mechanism includes a first member having a proximal end portion and a distal end portion and defining an inner volume therebetween, and a second member movably disposed in the inner volume of the first member. The distal end portion of the first member includes a first plunger including a flow channel configured to allow selective fluid communication between the inner volume defined by the housing and the inner volume defined by the first member. The second member includes a second plunger disposed at a distal end portion of the second member and an engagement portion configured to allow a user to selectively move the actuator mechanism.

In some embodiments, a syringe-based device for parenterally-procuring bodily fluid samples with reduced contamination from a patient includes a housing, an actuator mechanism, and a piercing member. The housing has a proximal end portion and a distal end portion and defines an inner volume therebetween. The proximal end portion is substantially open and the distal end portion has a port configured to be coupled to a lumen-defining device for receiving bodily fluids from the patient. The actuator mechanism is movably disposed in the inner volume of the housing. The actuator mechanism has a proximal end portion and a distal end portion and defining an inner volume therebetween. The distal end portion includes a plunger including a flow channel. The proximal end portion is substantially open and configured to receive a vacuum-sealed sample tube. The piercing member is disposed in the inner volume of the actuator mechanism and defines a lumen fluidically coupled to the flow channel of the plunger. The flow channel of the plunger and the piercing member configured to allow selective fluid communication between the inner volume defined by the housing and the inner volume defined by the actuator mechanism.

In some embodiments, a syringe-based device for parenterally-procuring bodily fluid samples with reduced contamination from a patient includes a housing, an actuator mechanism, and a flow control mechanism. The housing has a proximal end portion and a distal end portion and defines an inner volume therebetween. The proximal end portion is substantially open and the distal end portion has a port configured to be coupled to a lumen-defining device for receiving bodily fluids from the patient. The actuator mechanism is movably disposed in the inner volume of the housing and has a proximal end portion and a distal end portion. The distal end portion includes a first plunger and the proximal end portion including an engagement portion configured to allow a user to selectively move the actuator mechanism. A second plunger is movably disposed in the inner volume of the housing and releasably coupled to the actuator mechanism. The second plunger defines a flow channel configured to be placed in selective fluid communication with the port. The flow control mechanism is operable to selectively control fluid flow between the port and a pre-sample reservoir defined by the second plunger and the housing. The flow control mechanism is configured to be moved between a first configuration in which the bodily fluid can flow through a first flow path to the pre-sample reservoir, and a second configuration in which the bodily fluid can flow through a second flow path to a sample reservoir collectively defined by the first plunger, the second plunger, and the housing.

In some embodiments, a method of using a syringe-based transfer device, including a housing with a port and an actuator mechanism movably disposed in the housing, to obtain a bodily fluid sample from a patient includes establishing fluid communication between the patient and the port of the syringe-based transfer device and establishing fluid communication between the port and a pre-sample reservoir. A first volume of bodily fluid is transferred to the pre-sample reservoir with the syringe-based transfer device. The pre-sample reservoir is fluidically isolated from the port to sequester the first volume of bodily fluid in the pre-sample reservoir. After the first volume of bodily fluid has been sequestered in the pre-sample reservoir, fluid communication is established between the port and a sample reservoir defined at least in part by the actuator mechanism and the housing. The actuator mechanism is moved from a first position to a second position to draw a second volume of bodily fluid from the patient into the sample reservoir.

In some embodiments, an apparatus includes a housing and an actuator mechanism. The apparatus further includes a first fluid reservoir and a second fluid reservoir, fluidically isolated from the first fluid reservoir, defined at least in part by the housing and/or the actuator mechanism. The housing includes a port configured to receive a bodily-fluid. The housing and the actuator mechanism collectively define a first fluid flow path and a second fluid flow path. The first fluid flow path is configured to transfer a first flow of bodily-fluid from the port to the first fluid reservoir when the actuator mechanism is in a first position relative to the housing. The second fluid flow path is configured to transfer a second flow of bodily-fluid, substantially free from undesirable microbes that are not representative of in vivo patient condition, from the port to the second fluid reservoir when the actuator mechanism is in a second position relative to the housing.

In some embodiments, a bodily-fluid transfer device can be configured to selectively divert a first, predetermined amount of a flow of a bodily-fluid to a first reservoir before permitting the flow of a second amount of the bodily-fluid into a second reservoir. In this manner, the second amount of bodily-fluid can be used for diagnostic or other testing, while the first amount of bodily-fluid, which may contain microbes from a bodily surface and/or other external source, is isolated from the bodily-fluid to be tested for microbial presence but yet can be used for other blood tests as ordered by clinician (e.g., complete blood count "CBC", immunodiagnostic tests, cancer-cell detection tests, or the like).

As referred to herein, "bodily-fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used in this specification and the appended claims, the terms "first, predetermined amount," "first amount," and "first volume" describe an amount of bodily-fluid configured to be received or contained by a first reservoir or a pre-sample reservoir. While the terms "first amount" and "first volume" do not explicitly describe a predetermined amount, it should be understood that the first amount is the first, predetermined amount unless explicitly described differently.

As used in this specification and the appended claims, the terms "second amount" and "second volume" describe an amount of bodily-fluid configured to be received or contained by a second reservoir or sample reservoir. The second amount can be any suitable amount of bodily-fluid and need not be predetermined. Conversely, when explicitly described as such, the second amount received and contained by the second reservoir or sample reservoir can be a second, predetermined amount.

FIG. 1 is a schematic illustration of a portion of a syringe-based transfer device 100, according to an embodiment. Generally, the syringe-based transfer device 100 (also referred to herein as "bodily-fluid transfer device," "fluid transfer device," or "transfer device") is configured to permit the withdrawal of bodily-fluid from a patient such that a first portion or amount of the withdrawn fluid is fluidically isolated and diverted away from a second portion or amount of the withdrawn fluid that is to be used as a biological sample, such as for testing for the purpose of medical diagnosis and/or treatment. In other words, the transfer device 100 is configured to transfer a first, predetermined amount of a bodily-fluid to a first collection reservoir and a second amount of bodily-fluid to one or more bodily-fluid collection reservoirs (e.g., sample reservoirs) fluidically isolated from the first collection reservoir, as described in more detail herein.

The transfer device 100 includes a housing 101, an actuator mechanism 140, a first fluid reservoir 180 (also referred to herein as "first reservoir" or "pre-sample reservoir"), and a second fluid reservoir 190 (also referred to herein as "second reservoir" or "sample reservoir"), different from the first reservoir 180. The housing 101 can be any suitable shape, size, or configuration and is described in further detail herein with respect to specific embodiments. As shown in FIG. 1, the housing 101 includes a port 105 that can be at least temporarily physically and fluidically coupled to a medical device defining a pathway P for withdrawing and/or conveying the bodily-fluid from the patient to the transfer device 100. For example, the port 105 can be a Luer-Lok® or the like configured to be physically and fluidically coupled to a needle, a cannula, or other lumen-containing device. In other embodiments, the port 105 can be monolithically formed with at least a portion of the lumen-containing device. In this manner, the port 105 can receive the bodily-fluid from the patient via the pathway P as further described herein.

As shown in FIG. 1, the housing 101 defines an inner volume 111 that is configured to receive a portion of the actuator mechanism 140. More specifically, the actuator mechanism 140 is at least partially disposed within the inner volume 111 of the housing 101 and is movable between a first configuration and a second configuration relative to the housing 101. The housing 101 is also configured to house at least a portion of the first reservoir 180 and at least a portion of the second reservoir 190. For example, in some embodiments, the first reservoir 180 and/or the second reservoir 190 can be at least temporarily disposed within the inner volume 111 defined by the housing 101. In other embodiments, the first reservoir 180 and/or the second reservoir 190 can be at least partially defined by a set of walls of the housing 101 that define the inner volume 111. Similarly stated, a portion of the inner volume 111 can form at least a portion of the first reservoir 180 and/or a portion of the second reservoir 190.

The actuator mechanism 140 can be any suitable shape, size, or configuration. For example, in some embodiments, the shape and size of at least a portion of the actuator mechanism 140 substantially corresponds to the shape and size of the walls of the housing 101 defining the inner volumes 111. As described above, at least a portion of the actuator mechanism 140 is movably disposed within the inner volume 111 of the housing 101. For example, in some embodiments, a distal end portion of the actuator mechanism 140 is disposed within the inner volume 111 of the housing 101 and a proximal end portion of the actuator mechanism 140 is disposed substantially outside the housing 101. In this manner, a user can engage the proximal end portion of the actuator mechanism 140 to move the portion of the actuator mechanism 140 disposed within the inner volume 111 between the first configuration and the second configuration relative to the housing 101. In some embodiments, the actuator mechanism 140 can be disposed in a third configuration (or storage configuration) relative to the housing 101, as further described herein.

While not shown in FIG. 1, in some embodiments, the actuator mechanism 140 can include a first member and a second member. In such embodiments, both the first member and the second member can be collectively moved within the inner volume 111 of the housing 101. In addition, the first member and the second member can be configured to move independently within the housing 101. Similarly stated, the first member can be moved relative to the second member and/or the second member can be moved relative the first member, as further described below with respect to specific embodiments. In some embodiments, the first member and/or the second member can form a piston or plunger configured to move within the inner volume 111. Furthermore, a portion of the piston or plunger can form a substantially fluid tight seal with the walls of the housing 101 defining the inner volume 111. In this manner, the housing 101 and the actuator mechanism 140 can collectively form a sealed, air-tight cavity (e.g., a syringe) such that the actuator mechanism 140 (or at least a portion of the actuator mechanism 140) can be configured to introduce or otherwise facilitate the development of a vacuum within the inner volume 111.

The first reservoir 180 can be any suitable reservoir for containing the bodily-fluid. For example, in some embodiments, the first reservoir 180 is defined by a portion of the walls of the housing 101 defining the inner volume 111 and a portion of the actuator mechanism 140. In other embodiments, the first reservoir 180 is defined by only the actuator mechanism 140. In still other embodiments, the first reservoir 180 can be a pre-sample reservoir described in detail in U.S. Pat. No. 8,197,420 ("the '420 patent"), the disclosure of which is incorporated herein by reference in its entirety. In this manner, the first reservoir 180 can be selectively placed in fluid communication with the housing 101 or the actuator mechanism 140 either directly (e.g., physically and fluidically coupled to the housing 101 or the actuator mechanism 1400 or indirectly (e.g., fluidically coupled via intervening structure such as sterile flexible tubing).

The first reservoir 180 is configured to receive and contain the first, predetermined amount of the bodily-fluid. More specifically, when the actuator mechanism 140 is in the first configuration, a portion of the actuator mechanism 140 and a portion of the housing 101 can define a first fluid flow path 181 configured to fluidically couple the port 105 of the housing 101 to the first reservoir 180. In some embodiments, the actuator mechanism 140 can be moved to the first configuration (e.g., from the third configuration described above) and can introduce a vacuum that facilitates the flow of the bodily-fluid through the first flow path 181 and into the first reservoir 180. The first reservoir 180 is configured to contain the first amount of the bodily-fluid such that the first amount is fluidically isolated from a second amount of the bodily-fluid (different than the first amount of bodily-fluid) that is subsequently withdrawn from the patient.

The second reservoir 190 can be any suitable reservoir and is configured to receive and contain the second amount of the bodily-fluid. In some embodiments, the second reservoir 190 is defined by a portion of the walls of the housing 101 defining the inner volume 111 and a portion of the actuator member 140. In this manner, when the actuator mechanism 140 is in the second configuration, a portion of the actuator mechanism 140 and a portion of the housing 101 can define a second fluid flow path 191 configured to fluidically couple the port 105 to the second reservoir 190. In some embodiments, the movement of the actuator mechanism 140 to the second configuration can be such that a second vacuum force facilitates the flow of the bodily-fluid through the second flow path 191 and into the second reservoir 190. The second amount of bodily-fluid can be an amount withdrawn from the patient subsequent to withdrawal of the first amount. In some embodiments, the second reservoir 190 is configured to contain the second amount of the bodily-fluid such that the second amount is fluidically isolated from the first amount of the bodily-fluid.

As described above, the transfer device 100 can be used to transfer a bodily-fluid from a patient to the first reservoir 180 and/or second reservoir 190 included in the transfer device 100. More specifically, the flow of the first amount of bodily-fluid transferred to the first reservoir 180 can be such that dermally-residing microbes dislodged during a venipuncture event and/or other external sources (e.g. ambient airborne microbes, transferred from the skin of the practitioner collecting the sample, etc.) become entrained in the flow and are thereby transferred to the first reservoir 180. In addition, the first reservoir 180 fluidically isolates the first amount such that when the subsequent second amount is withdrawn into the second reservoir 190, the second amount is substantially free from the dermally-residing microbes. Although not shown in FIG. 1, in some embodiments, the syringe-based transfer device 100 can be coupled to a device in fluid communication with the patient that is also configured to reduce contamination of a patient sample. For example, in some embodiments, the syringe-based transfer device 100 can be used with a lumenless needle or the like such as those described in U.S. Patent Application Ser. No. 61/777,758, entitled "Lumenless Needle for Bodily-Fluid Sample Collection," filed on Mar. 12, 2013 ("the '758 application") the disclosure of which is incorporated herein by reference in its entirety.

In some embodiments, the transfer device 100 can be configured such that the first amount of bodily-fluid need be conveyed to the first reservoir 180 before the transfer device 100 will permit the flow of the second amount of bodily-fluid to be conveyed through the second flow path 191 to the second reservoir 180. In this manner, the transfer device 100 can be characterized as requiring compliance by a health care practitioner regarding the collection of the first, predetermined amount (e.g., a pre-sample) prior to collection of the second amount (e.g., a sample) of bodily-fluid. Similarly stated, the transfer device 100 can be configured to prevent a health care practitioner from collecting the second amount, or the sample, of bodily-fluid into the second reservoir 190 without first diverting the first amount, or pre-sample, of bodily-fluid into the first reservoir 180. In this manner, the health care practitioner is prevented from including (whether intentionally or unintentionally) the first amount of bodily-fluid, which is more likely to contain dermally-residing microbes and/or other external undesirable contaminants, in the bodily-fluid sample to be used for analysis. In other embodiments, the fluid transfer device 100 need not include a forced-compliance feature or component.

In some embodiments, the actuator mechanism 140 can have a fourth configuration, different than the first, second, and third configurations. In such embodiments, the actuator mechanism 140 can be moved toward, the fourth configuration when the transfer device 100 has collected the second amount of the bodily-fluid and has been removed from contact with the patient. When in the fourth configuration, the first fluid reservoir 180 can maintain the first amount of bodily-fluid in fluid isolation and the second fluid reservoir 190 can be maintained in fluid communication with the port 105. Therefore, when the actuator mechanism 140 is moved toward the fourth configuration the transfer device 100 can transfer a portion of the second amount of the bodily-fluid from the second reservoir 190 to any suitable container (e.g., a vile, a test tube, a petri dish, a culture medium, a test apparatus, or the like) such that the portion of the second amount of bodily-fluid can be tested.

FIGS. 2-6 illustrate a syringe-based transfer device 200 according to an embodiment. The syringe-based transfer device 200 (also referred to herein as "bodily-fluid transfer device," "fluid transfer device," or "transfer device") includes a housing 201 and an actuator mechanism 240. Furthermore, the transfer device 200 is configured to include or define a first fluid reservoir 280 (also referred to herein as "first reservoir" or "pre-sample reservoir") and a second fluid reservoir 290 (also referred to herein as "second reservoir" or "sample reservoir"). The transfer device 200 can be any suitable shape, size, or configuration. For example, while shown in FIGS. 2 and 3 as being substantially cylindrical, the transfer device 200 can be square, rectangular, polygonal, and/or any other non-cylindrical shape.

Figure 2:
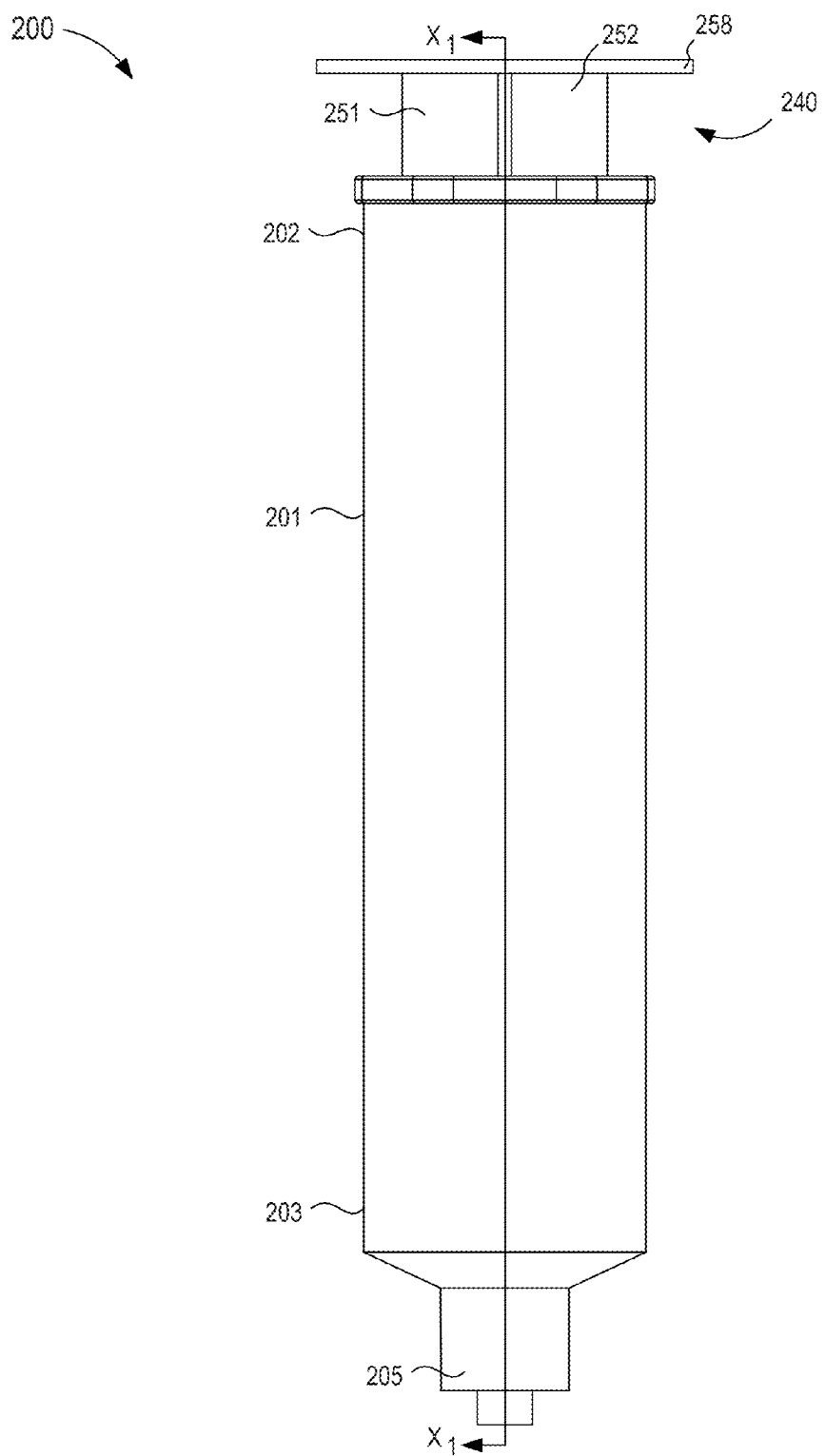
FIG. 2 is a front view of a syringe-based transfer device according to an embodiment, in a first configuration.
Figure 3:
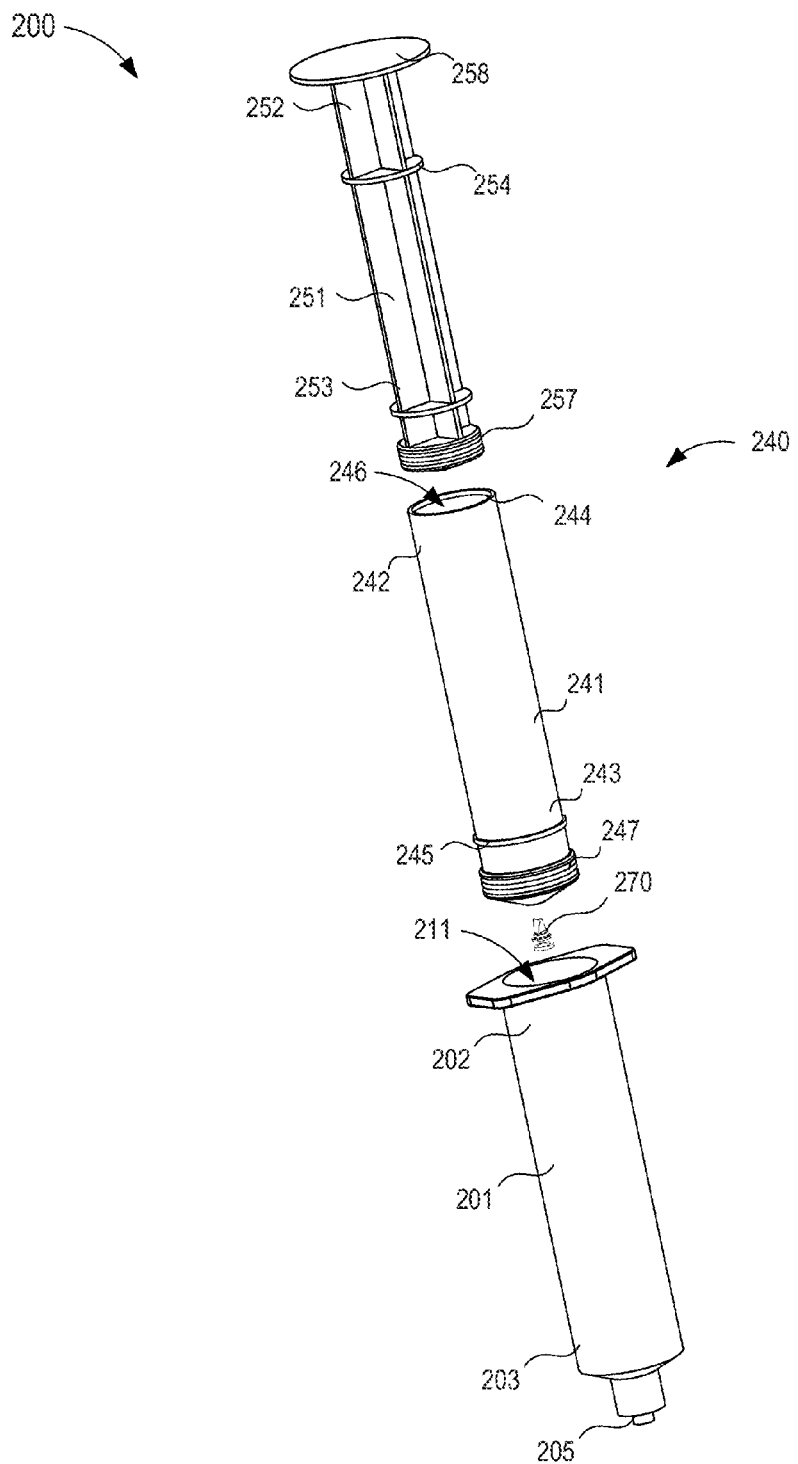
FIG. 3 is an exploded view of the syringe-based transfer device of FIG. 2.
Figure 4:
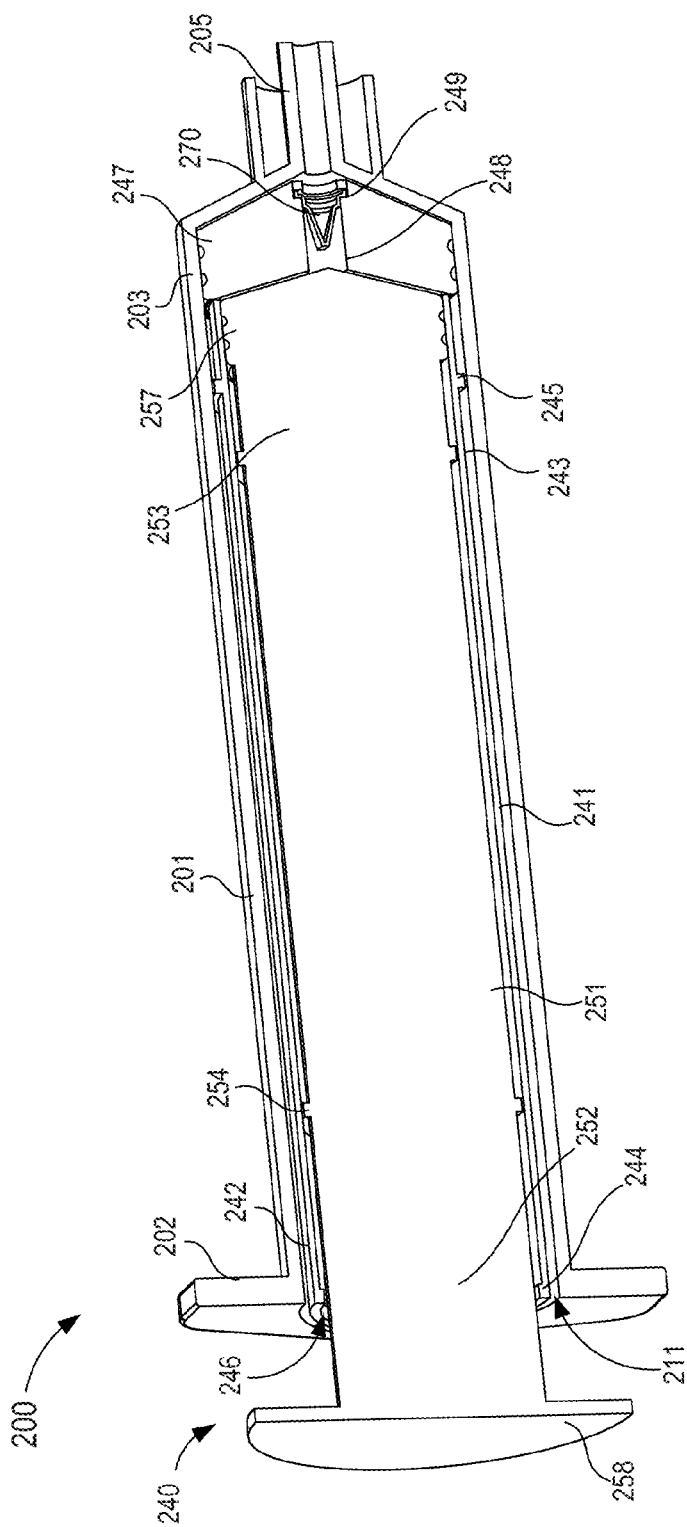
FIG. 4 is a cross-sectional view of the syringe-based transfer device illustrated in FIG. 2 taken along the line $X_1$-$X_1$, in the first configuration.

As shown in FIGS. 2 and 3, the housing 201 includes a proximal end portion 202 and a distal end portion 203 and defines an inner volume 211 therebetween. In some embodiments, the housing 201 can be substantially similar to a syringe body. The proximal end portion 202 of the housing 201 is substantially open and is configured to receive at least a portion of the actuator mechanism 240 such that the portion of the actuator mechanism 240 is movably disposed within the inner volume 211. Furthermore, the inner volume 211 is configured to define the second fluid reservoir 290, as further described herein. The distal end portion 203 of the housing 201 includes a port 205. In some embodiments, the port 205 can be monolithically formed with the housing 201 (e.g., as shown in FIGS. 2-6). In other embodiments, the port 205 can be coupled to the distal end portion 203 in any suitable manner such as, for example, via a friction fit, a threaded coupling, a mechanical fastener, an adhesive, any number of mating recesses, and/or any combination thereof.

The port 205 can be any suitable shape, size, or configuration. For example, in some embodiments, at least a portion of the port 205 can form a lock mechanism configured to be physically and fluidically coupled to a needle, a cannula, or other lumen-containing device. For example, in some embodiments, the port 205 can be a Luer-Lok® or similar locking mechanism configured to physically and fluidically couple to a needle or cannula assembly (not shown in FIGS. 2-6). In other embodiments, the port 205 can be monolithically formed with at least a portion of the lumen-containing device. In this manner, the port 205 can be placed in fluid communication with a lumen defined by the lumen-defining device and to receive the bodily-fluid from a patient when the lumen-defining device is disposed within the patient (e.g., as a result of a venipuncture event), as further described herein.

As described above, the actuator mechanism 240 is disposed within the inner volume 211 and is movable between a first position (e.g., a distal position relative to the housing 201) and a second position (e.g., a proximal position relative to the housing 201). Furthermore, the movement of the actuator mechanism 240 relative to the housing 201 can move the transfer device 200 between a first, second, and third configuration, as further described herein. The actuator mechanism 240 includes a first member 241 and a second member 251. The first member 241 of the actuator mechanism 240 includes a proximal end portion 242 and a distal end portion 243 and defines an inner volume 246 therebetween. At least a portion of the inner volume 246 is configured to define the first reservoir 280, as further described herein.

The proximal end portion 242 is substantially open such that at least a portion of the second member 251 can be movably disposed within the inner volume 246. The proximal end portion 242 also includes a protrusion 244 that extends from an inner surface of a wall (or set of walls) defining the inner volume 246 and is configured to selectively engage a portion of the second member 251.

The distal end portion 243 of the first member 241 includes a plunger 247. The plunger 247 is configured to form a friction fit with the inner surface of the walls defining the inner volume 211 when the actuator mechanism 240 is disposed within the housing 201. Similarly stated, the plunger 247 defines a fluidic seal with the inner surface of the walls defining the inner volume 211 such that a portion of the inner volume 211 proximal of the plunger 247 is fluidically isolated from a portion of the inner volume 211 distal of the plunger 247. The plunger 247 is further configured to define a channel 248 that extends though a distal end and a proximal end of the plunger 247. Moreover, a portion of an inner set of walls defining the channel 248 is configured to form a valve seat 249. In this manner, a portion of the channel 248 can receive a valve 270 that is in contact with the valve seat 249.

The valve 270 can be any suitable valve. For example, in some embodiments, the valve 270 is a one-way check valve configured to allow a flow of a fluid from a distal end of the valve 270 to a proximal end of the valve 270 but substantially not allow a flow of the fluid from the proximal end to the distal end. In addition, the valve 270 can be disposed within the channel 248 and can be in contact with the valve seat 249 such that the valve 270 forms a substantially fluid tight seal with the walls defining the channel 248. In some embodiments, the valve 270 can form a first fit with walls defining the channel 248. In other embodiments, the valve 270 can form a threaded coupling or the like with at least a portion of the walls. The valve 270 can also include a seal member configured to engage the valve seat 249 thereby forming at least a portion of the fluid tight seal. The arrangement of the plunger 247 and the valve 270 is such that when the valve 270 is in the open configuration, the inner volume 246 defined by the first member 241 is placed in fluid communication with the portion of the inner volume 211 of the housing 201 that is distal of the plunger 247, as further described herein.

The second member 251 of the actuator mechanism 240 includes a proximal end portion 252 and a distal end portion 253. The proximal end portion 252 includes an engagement portion 258 that can be engaged by a user (e.g., a phlebotomist, a nurse, a technician, a physician, etc.) to move at least a portion of the actuator mechanism 240 relative to the housing 201. The distal end portion 253 includes a plunger 257 configured to form a friction fit with the inner surface of the walls defining the inner volume 246 when the second member 251 is disposed with the first member 241. Similarly stated, the plunger 257 defines a fluidic seal with the inner surface of the walls defining the inner volume 246 such that a portion of the inner volume 246 proximal of the plunger 257 is fluidically isolated from a portion of the inner volume 246 distal of the plunger 257.

As described above, at least a portion the second member 251 is configured to be movably disposed within the inner volume 246 of the first member 241. More specifically, the second member 251 can be movable between a first position (e.g., a distal position) and a second position (e.g., a proximal position) thereby moving the actuator mechanism 240 between a first configuration and a second configuration, respectively. In addition, the second member 251 includes a protrusion 254 that extends in a radial direction to selectively engage the protrusion 244 of the first member 241. In this manner, the protrusion 244 of the first member 241 and the protrusion 254 of the second member 251 can be placed in contact to substantially limit a proximal movement of the second member 251 relative the first member 241.

In use, a user can engage the transfer device 200 to couple the port 205 to a proximal end portion of a lumen-defining device (not shown) such as, for example, a butterfly needle, a cannula assembly, a trocar (which is some cases is used to insert a catheter into a patient), or the like. With the port 205 physically coupled to the lumen-defining device, the port 205 is placed in fluid communication with the lumen defined by the lumen-defining device. Furthermore, the distal end portion of the lumen-defining device can be disposed within a portion of the body of a patient (e.g., a vein). In this manner, the port 205 is placed in fluid communication with the portion of the body.

With the port 205 coupled to the lumen-defining device, a user (e.g., a phlebotomist, a nurse, a technician, a physician, or the like) can move the transfer device 200 from the first configuration to the second configuration. More specifically, the user can engage the engagement portion 258 of the second member 251 included in the actuator mechanism 240 to move the actuator mechanism 240 from its first configuration to its second configuration, thereby placing the transfer device 200 in the second configuration, as indicated by the arrow AA in FIG. 5. In this manner, the second member 251 of the actuator mechanism 240 is moved in a proximal direction relative to the first member 241 (e.g., the first member 241 does not substantially move in the proximal direction) until the protrusion 254 of the second member 251 is placed into contact with the protrusion 244 of the first member 241.

The arrangement of the second member 251 within the first member 241 is such that the proximal motion of the second member 251 increases the volume of the portion of the inner volume 246 that is distal of the plunger 257, thereby defining the first reservoir 280. Furthermore, with the plunger 257 forming a fluid tight seal with the inner surface of the walls defining the inner volume 246, the increase of volume can produce a negative pressure within the first reservoir 280.

Figure 5:
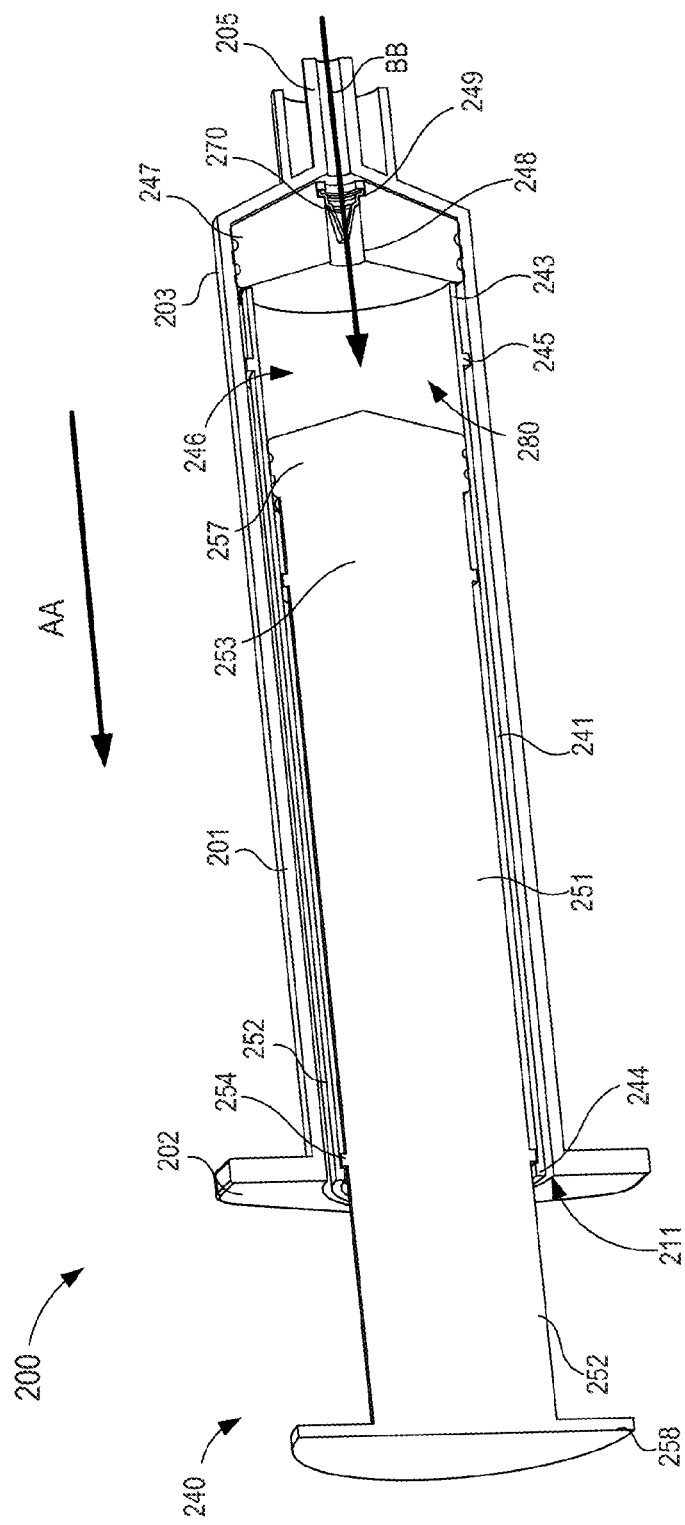
FIG. 5 is a cross-sectional view of the syringe-based transfer device of FIG. 2 taken along the line $X_1$-$X_1$, in a second configuration.

As shown by the arrow BB in FIG. 5, the port 205, the valve 270, and the channel 248 define a fluid flow path that places the first reservoir 280 in fluid communication with the lumen-defining device. Therefore, the first reservoir 280 is placed in fluid communication with the portion of the patient (e.g., the vein). Expanding further, the negative pressure within the first reservoir 280 can be operative in moving the valve 270 from a closed configuration to an open configuration. In this manner, the negative pressure within the within the first reservoir 280 produced by the movement of the plunger 257 introduces a suction force within the portion of the patient. Thus, a bodily-fluid is drawn through the port 205 and the valve 270 and into the first reservoir 280. In some embodiments, the bodily-fluid can contain undesirable microbes such as, for example, dermally-residing microbes and/or other external contaminants.

In some embodiments, the magnitude of the suction force can be modulated by increasing or decreasing the amount of a force applied to the actuation mechanism 240. For example, in some embodiments, it can be desirable to limit the amount of suction force introduced to a vein. In such embodiments, the user can reduce the amount of force applied to the engagement portion 258 of the second member 251. In this manner, the rate of change (e.g., the increase) in the volume of the first reservoir 280 can be sufficiently slow to allow time for the negative pressure differential between the vein and the fluid reservoir to come to equilibrium before further increasing the volume of the first reservoir 280. Thus, the magnitude of the suction force can be modulated.

While in the second configuration, the transfer device 200 can be configured to transfer a desired amount (e.g., a predetermined amount) of bodily-fluid transferred to the first reservoir 280. In some embodiments, the first, predetermined amount can substantially correspond to the size of the first reservoir 280. In other embodiments, the first amount can substantially correspond to an equalization of pressure within the first reservoir 280 and the portion of the patient. Moreover, in such embodiments, the equalization of the pressure can be such that the valve 270 is allowed to return to the closed configuration. Thus, the first reservoir 280 is fluidically isolated from a volume substantially outside the first reservoir 280.

With the first amount fluidically isolated, the actuator mechanism 240 can be moved from the second configuration to a third configuration by further moving the actuator mechanism 240 in the proximal direction. For example, as indicated by the arrow CC in FIG. 6, the user can apply a force to the engagement portion 258 of the second member 251 to move the actuator mechanism 240 relative to the housing 201. Expanding further, with the protrusion 254 of the second member 251 in contact with the protrusion 244 of the first member 241, the further application of force on the engagement portion 258 is such that the first member 241 and the second member 251 collectively move in the proximal direction relative to tie housing 201.

The arrangement of the first member 241 within the inner volume 211 of the housing 201 is such that the proximal motion of the first member 241 increases the volume of the portion of the inner volume 211 that is distal of the plunger 247, thereby defining the second reservoir 290. Furthermore, with the plunger 247 forming a fluid tight seal with the inner surface of the walls defining the inner volume 211 and with the valve 270 in the closed configuration, the increase of volume can produce a negative pressure within the second reservoir 290.

Figure 6:
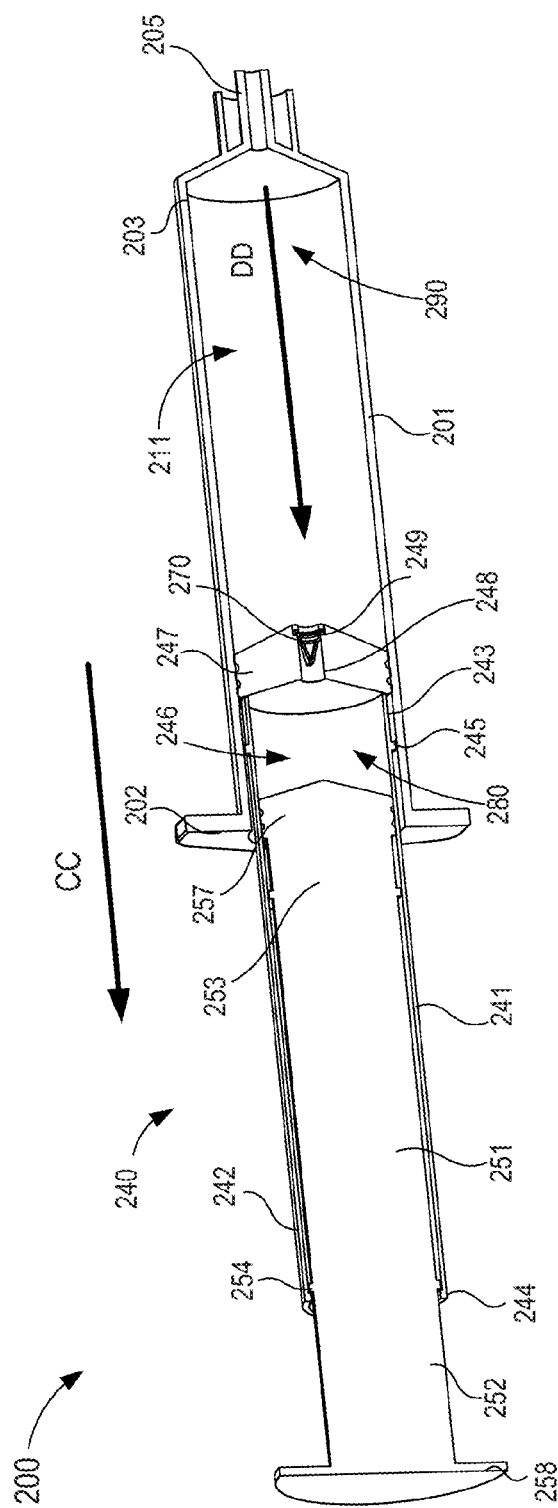
FIG. 6 is a cross-sectional view of the syringe-based transfer device of FIG. 2 taken along the line $X_1$-$X_1$, in a third configuration.

As shown by the arrow DD in FIG. 6, the port 205 and a portion of the inner volume 211 define a fluid flow path that places the second reservoir 290 in fluid communication with the lumen-defining device. Therefore, the second reservoir 290 is placed in fluid communication with the portion of the patient (e.g., the vein). Expanding further, the negative pressure within the second reservoir 290 produced by the movement of the plunger 247 introduces a suction force within the portion of the patient. Thus, a bodily-fluid is drawn through the port 205 and into the second reservoir 290. In addition, the bodily-fluid contained within the second reservoir 290 is substantially free from microbes generally found outside of the portion of the patient (e.g., dermally residing microbes, microbes within a lumen defined by the transfer device 200, microbes within the lumen defined by the lumen defining device, and/or any other undesirable microbe).

While not shown in FIGS. 2-6, the actuator mechanism 240 can be moved from the third configuration to a fourth configuration to place the transfer device 200 in a fourth configuration. For example, in some embodiments, with the desired amount of bodily-fluid disposed within the second fluid reservoir 290, the transfer device 200 can be removed from the portion of the patient and disposed above or in a container (e.g., a vile, a test tube, a petri dish, a culture medium, a test apparatus, a cartridge designed for use with an automated, rapid microbial detection system, or the like) such that at least a portion of the second amount of bodily-fluid can be tested. The withdrawn bodily-fluid can be used for any number of testing processes or procedures such as, for example, blood culture testing, real-time diagnostics, and/or PCR-based approaches. Expanding further, the user can apply a force to the engagement portion 258 of the second member 251 to move the actuator mechanism 240 in the distal direction (e.g., opposite the arrow CC shown in FIG. 6). With the valve 270 in the closed configuration the bodily-fluid contained within the first reservoir 280 is maintained in fluid isolation with a volume outside the first reservoir 280. In some embodiments, the volume of the first reservoir 280 is sufficient to contain the first centiliter or few centiliters of bodily-fluid. In other embodiments, the first reservoir 280 can be configured to contain from about 0.1 ml to about 3.0 ml. In still other embodiments, the first reservoir 280 can be configured to contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. Furthermore, the pressure within the first reservoir 280 can be such that the force applied to the second member 251 does not substantially move the second member 251 relative to the first member 241. Thus, the force applied to the engagement portion 258 collectively moves the second member 251 and the first member 241 in the distal direction relative to the housing 201 to expel a desired portion of the second amount of bodily-fluid from the lumen-defining device and into the container.

Although not shown in FIGS. 2-6, in some embodiments, the syringe-based transfer device 200 can be coupled to a device in fluid communication with the patient that is also configured to reduce contamination of a patient sample. For example, in some embodiments, the syringe-based transfer device 200 can be used with a lumenless needle or the like such as those described in the '758 application.

FIGS. 7-10 illustrate a syringe-based transfer device 300 according to an embodiment. The syringe-based transfer device 300 (also referred to herein as "bodily-fluid transfer device," "fluid transfer device," or "transfer device") is configured to be moved between a first, second, third, and fourth configuration, as further described herein. The transfer device 300 includes a housing 301 and an actuator 341. Furthermore, the transfer device 300 is configured to include or define a first fluid reservoir 380 (also referred to herein as "first reservoir" or "pre-sample reservoir") and a second fluid reservoir 390 (also referred to herein as "second reservoir" or "sample reservoir"). The transfer device 300 can be any suitable shape, size, or configuration. For example, while shown in FIGS. 7 and 8 as being substantially cylindrical, the transfer device 300 can be square, rectangular, polygonal, and/or any other non-cylindrical shape. Moreover, portions of the transfer device 300 can be substantially similar to the corresponding portions of the transfer device 200, described above in reference to FIGS. 2-6. Therefore, such portions are not described in further detail herein and should be considered substantially similar unless explicitly described differently.

Figure 7:
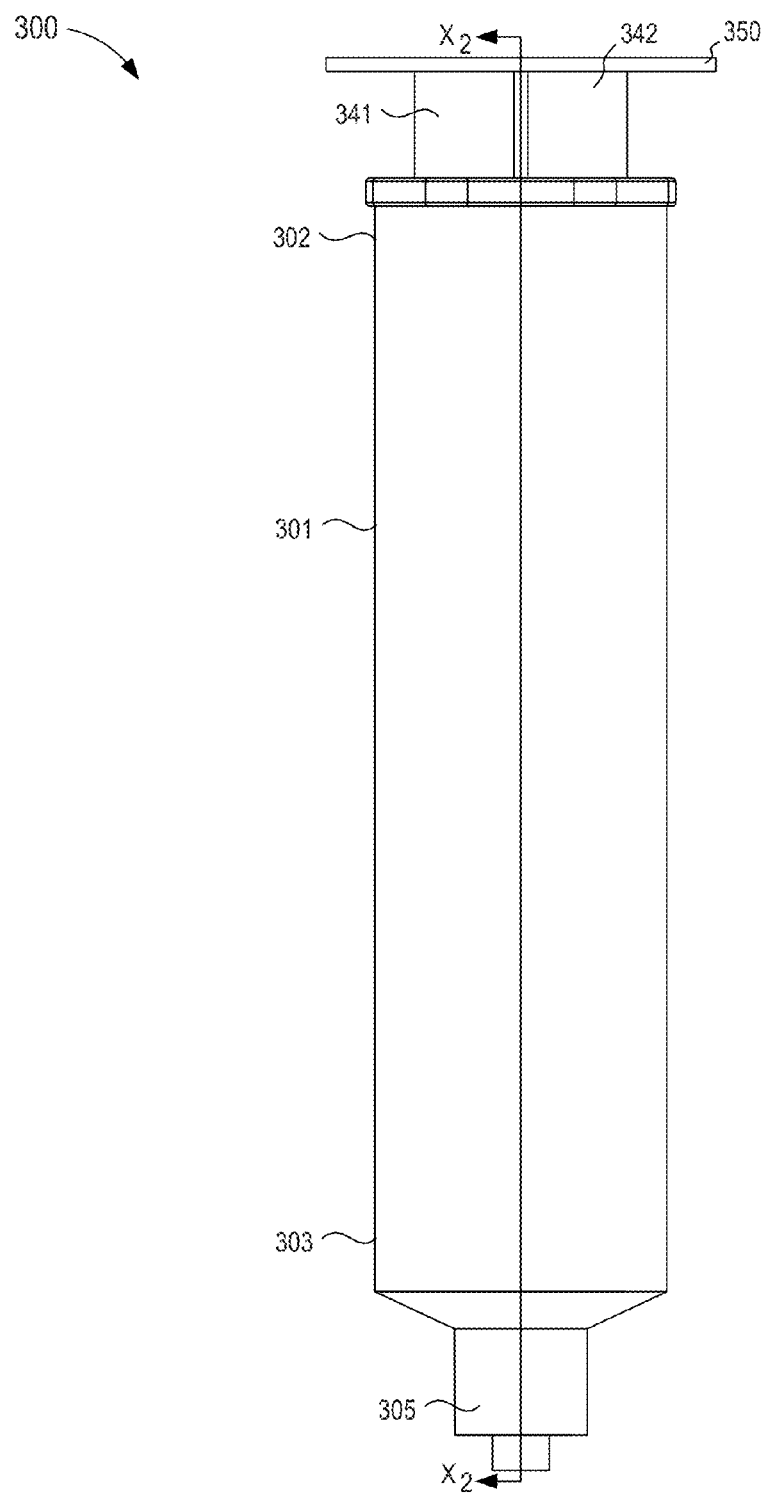
FIG. 7 is a front view of a syringe-based transfer device according to an embodiment, in a first configuration.
Figure 8:
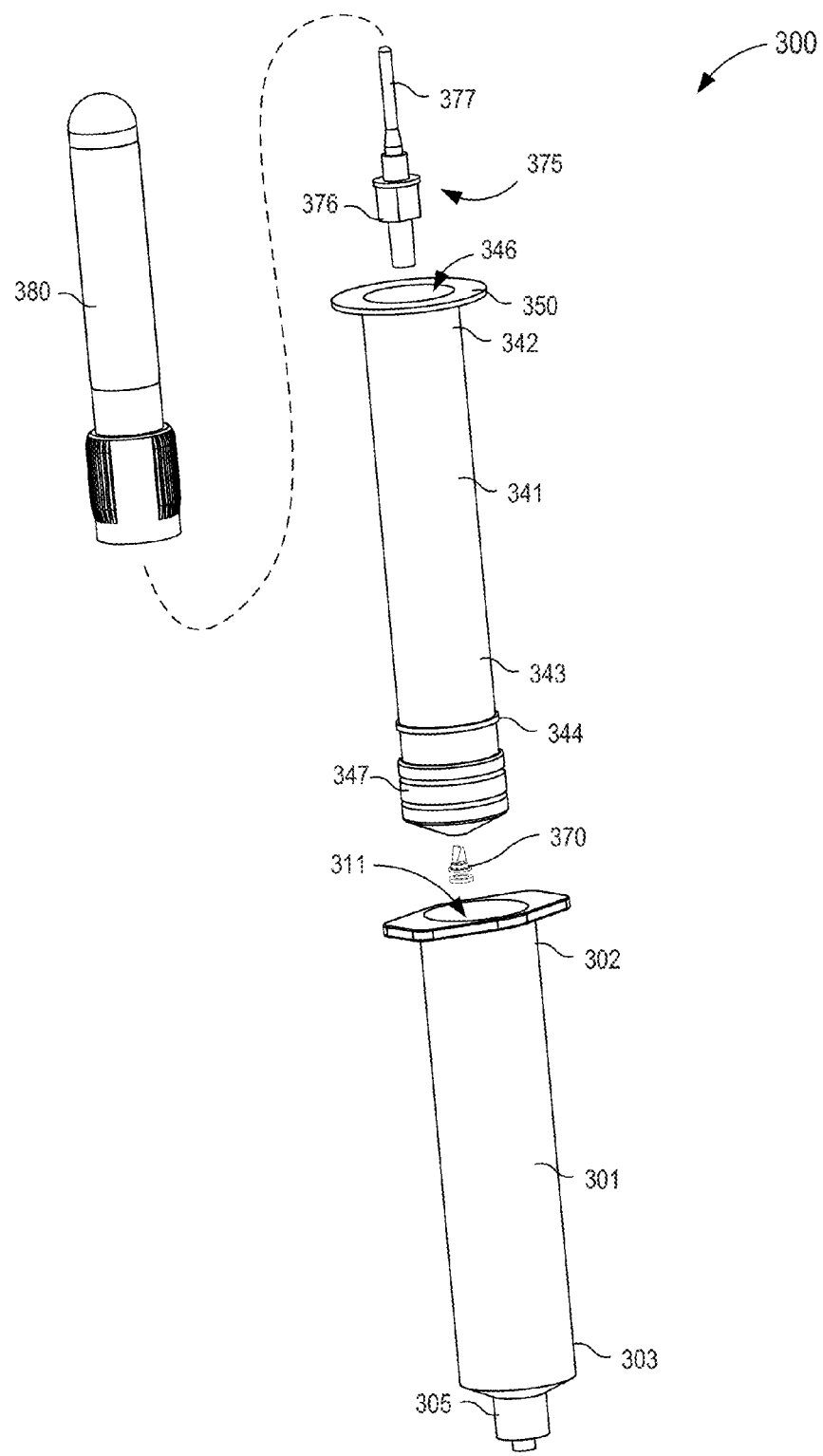
FIG. 8 is an exploded view of the syringe-based transfer device of FIG. 7.

As shown in FIGS. 7 and 8, the housing 301 includes a proximal end portion 302 and a distal end portion 303 and defines an inner volume 311 therebetween. The proximal end portion 302 of the housing 301 is substantially open and is configured to receive at least a portion of the actuator 341 such that the portion of the actuator 341 is movably disposed within the inner volume 311. Furthermore, the inner volume 311 is configured to define the second fluid reservoir 390, as further described herein. The distal end portion 303 of the housing 301 includes a port 305. The port 305 is configured to be coupled to or monolithically formed with a lumen-containing device, such as those described above.

As described above, the actuator 341 is disposed within the inner volume 311 and is movable between a first position (e.g., a distal position relative to the housing 301) and a second position (e.g., a proximal position relative to the housing 301). The actuator 341 includes a proximal end portion 342 and a distal end portion 343 and defines an inner volume 346 therebetween. The proximal end portion 342 includes an engagement portion 350, as described above with respect to the second member 251 of the actuator mechanism 240. In addition, the proximal end 342 is substantially open such that at least a portion of the first reservoir 380 can be movably disposed within the inner volume 346.

The distal end portion 343 of the actuator 341 includes a plunger 347. The plunger 347 is configured to form a friction fit with the inner surface of the walls defining the inner volume 311 when the actuator 341 is disposed within the housing 301, as described in detail above in reference FIGS. 2-6. The plunger 347 also defines a channel 348 that extends though a distal end and a proximal end of the plunger 347. The channel 348 is configured to receive a port 375 having a base 376 and a piercing member 377. The base 376 can be disposed within the channel 348 and forms a friction fit with a set walls defining the channel 348. In this manner, the base 376 and the walls defining the channel 348 can form a substantially fluid tight seal. The piercing member 377 of the port 375 is configured to extend in the proximal direction from the base 376. As shown in FIG. 8, the piercing member 377 can be disposed within a sheath configured to be selectively moved to expose, for example, a needle. For simplicity, FIGS. 8-10 only illustrate a sheath of the piercing member and not the needle disposed therein.

A portion of the set of walls defining the channel 348 is configured to form a valve seat 349. In this manner, a portion of the channel 348 can receive a valve 370 such that the valve 370 is in contact with the valve seat 349. The valve 370 can be any suitable configuration, for example, the valve 370 can be similar in form and function to the valve 270 described above. In this manner, the arrangement of the plunger 347 and the valve 370 is such that when the valve 370 is in the open configuration, the port 375 is placed in fluid communication with the portion of the inner volume 311 of the housing 301 that is distal of the plunger 347, as further described herein.

In use, a user can engage the transfer device 300 to couple the port 305 to a proximal end portion of a lumen-defining device (not shown) such as, for example, a butterfly needle, a cannula assembly, a trocar (which in some cases is used to insert a catheter into a patient), or the like. With the port 305 physically coupled to the lumen-defining device, the port 305 is placed in fluid communication with the lumen defined by the lumen-defining device. Furthermore, the distal end portion of the lumen-defining device can be disposed within a portion of the body of a patient (e.g., a vein). In this manner, the port 305 is placed in fluid communication with the portion of the body.

With the port 305 coupled to the lumen-defining device, a user (e.g., a phlebotomist, a nurse, a technician, a physician, or the like) can move the transfer device 300 from the first configuration to the second configuration. In this manner, the user can engage the first reservoir 380 and place the first reservoir 380 within the inner volume 346 defined by the actuator 341. More specifically, as shown in FIG. 8, the first reservoir 380 can be an external fluid reservoir configured to receive a fluid. For example, in some embodiments, the first reservoir 380 can be a Vacutainer® and/or a monolithically formed chamber in the transfer device 300) with or without a negative pressure. In other embodiments, the first reservoir 380 can be a pre-sample reservoir such as those disclosed in the '420 patent. In this manner, the first reservoir 380 can be placed within the inner volume 346 of the actuator 341, as indicated by the arrow EE in FIG. 9.

The insertion of the first reservoir 380 into the inner volume 346 of the actuator 341 can place the transfer device 300 in the second configuration. Furthermore, the distal end portion of the first reservoir 380 can be configured to include a pierceable septum that can receive the piercing member 377 of the port 375. While not shown in FIG. 9, the distal end portion of the first reservoir 380 can engage the port 375 such that the sheath of the piercing member 377 is moved, thereby exposing the needle. Thus, the needle can pierce the septum of the first reservoir 380 to place the first reservoir 380 in fluid communication with the port 375. The arrangement of the first reservoir 380 can also be such that the inner volume defined therein is substantially evacuated. Similarly stated, the inner volume of the first reservoir 380 defines a negative pressure.

Figure 9:
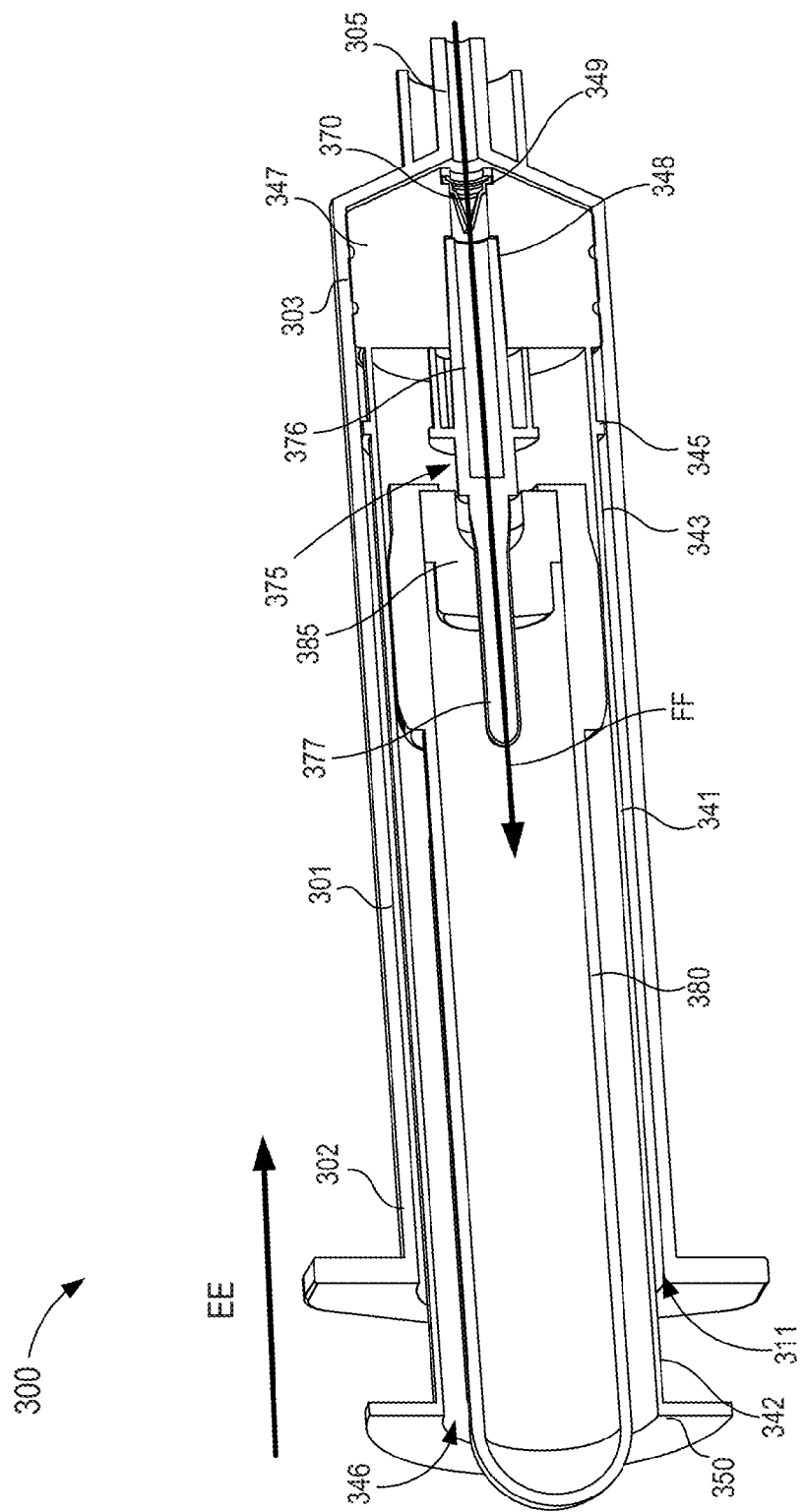
FIG. 9 is a cross-sectional view of the syringe-based transfer device of FIG. 7 taken along the line $X_2$-$X_2$, in the first configuration.

As shown by the arrow FF in FIG. 9, the port 305, the valve 370, and the port 375 define a fluid flow path such that the first reservoir 380 is in fluid communication with the lumen-defining device. Therefore, the first reservoir 380 is placed in fluid communication with the portion of the patient (e.g., the vein, the spinal cavity, etc.). Expanding further, the negative pressure within the first reservoir 380 can be operative in moving the valve 370 from a closed configuration to an open configuration. In this manner, the negative pressure within the within the first reservoir 380 introduces a suction force within the portion of the patient. Thus, a bodily-fluid is drawn through the port 305, the valve 370, and the port 375 and into the first reservoir 380. In some embodiments, the bodily-fluid can contain undesirable microbes such as, for example, dermally-residing microbes and/or other external contaminants.

While in the second configuration, the transfer device 300 can be configured to transfer a desired amount (e.g., a predetermined amount) of bodily-fluid transferred to the first reservoir 380. In some embodiments, the first, predetermined amount can substantially correspond to an equalization of pressure within the first reservoir 380 and the portion of the patient. Moreover, in such embodiments, the equalization the pressure can be such that the valve 370 is allowed to return to the closed configuration. Thus, the first reservoir 380 is fluidically isolated from a volume substantially outside the first reservoir 380.

With the first amount of bodily-fluid (e.g., the amount containing dermally-residing microbes) fluidically isolated, the first reservoir 380 can be removed from the inner volume 346 of the actuator 341 and discarded. In this manner, the actuator 341 can be moved from the second configuration to a third configuration by moving the actuator 341 in the proximal direction. For example, as indicated by the arrow GG in FIG. 10, the user can apply a force to the engagement portion 350 of the actuator 341 to move the actuator 341 relative to the housing 301. The arrangement of the actuator 341 within the inner volume 311 of the housing 301 is such that the proximal motion of the actuator 341 increases the volume of the portion of the inner volume 311 that is distal of the plunger 347, thereby defining the second reservoir 390. Furthermore, with the plunger 347 forming a fluid tight seal with the inner surface of the walls defining the inner volume 311 and with the valve 370 in the closed configuration, the increase of volume can produce a negative pressure within the second reservoir 390.

Figure 10:
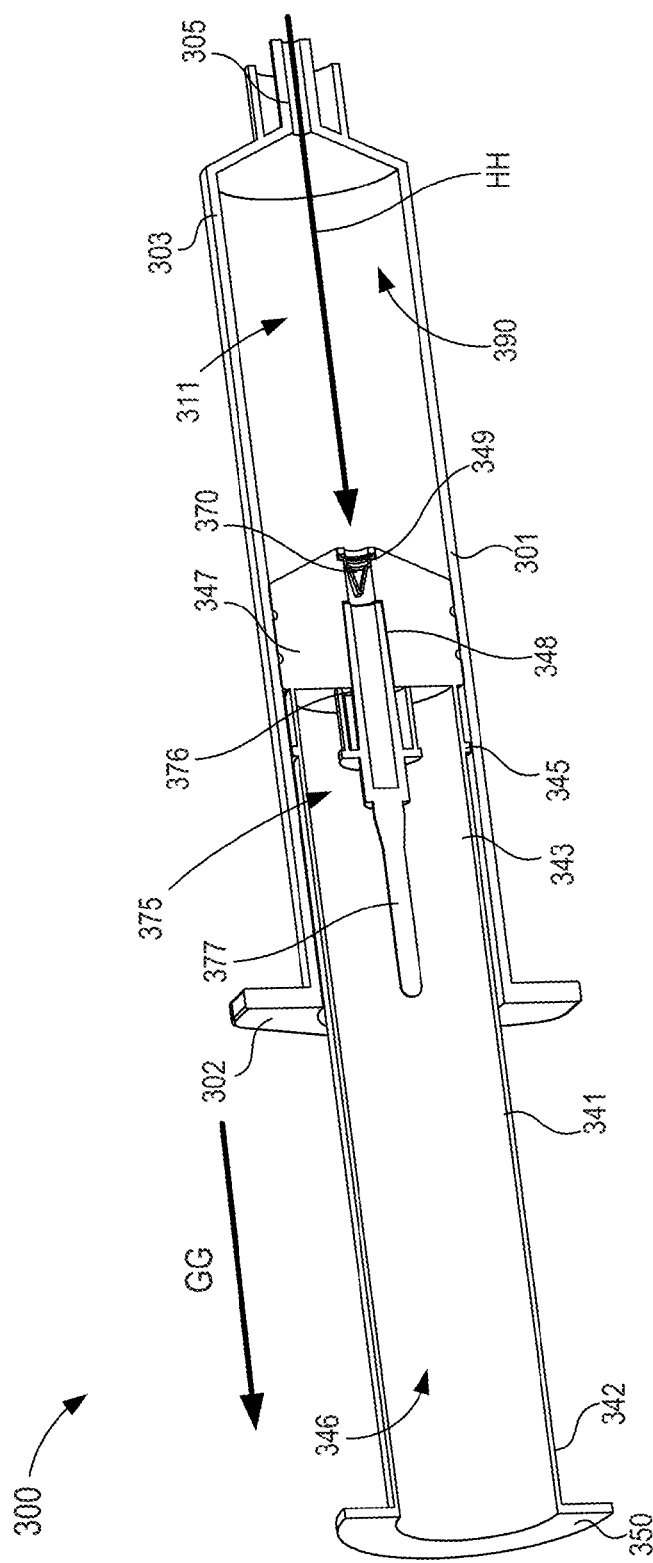
FIG. 10 is a cross-sectional view of the syringe-based transfer device of FIG. 7 taken along the line $X_2$-$X_2$, in a second configuration.

As shown by the arrow HH in FIG. 10, the port 305 and a portion of the inner volume 311 define a fluid flow path such that the second reservoir 390 is in fluid communication with the lumen-defining device. Therefore, the second reservoir 380 is placed in fluid communication with the portion of the patient (e.g., the vein, spinal cavity, etc.). Expanding further, the negative pressure within the second reservoir 390 produced by the movement of the plunger 347 introduces a suction force within the portion of the patient. Thus, a bodily-fluid is drawn through the port 305 and into the second reservoir 390. In addition, the bodily-fluid contained within the second reservoir 390 is substantially free from microbes generally found outside of the portion of the patient (e.g., dermally residing microbes, microbes within a lumen defined by the transfer device 300, microbes within the lumen defined by the lumen defining device, and/or any other undesirable microbe). Although not shown in FIGS. 7-10, in some embodiments, the syringe-based transfer device 300 can be coupled to a device in fluid communication with the patient that is also configured to reduce contamination of a patient sample. For example, in some embodiments, the syringe-based transfer device 300 can be used with a lumenless needle or the like such as those described in the '758 application.

While not shown in FIGS. 7-10, the actuator 341 can be moved from the third configuration to a fourth configuration to place the transfer device 300 in a fourth configuration. For example, in some embodiments, with the desired amount of bodily-fluid disposed within the second fluid reservoir 390, the transfer device 300 can be removed from the portion of the patient and disposed above or in a container (e.g., a vile, a test tube, a petri dish, a culture medium, a test apparatus, a cartridge or the like) such that a portion of the second amount of bodily-fluid can be tested. Expanding further, the user can apply a force to the engagement portion 350 to move the actuator 341 in the distal direction. Therefore, with the valve 370 in the closed configuration the force applied to the engagement portion 350 the actuator 341 in the distal direction relative to the housing 301 to expel a desired portion of the second amount of bodily-fluid from the lumen-defining device and into the container.

While the embodiments shown above describe an actuator being operative in directing a flow of a bodily-fluid, in some embodiments, a transfer device can include a flow control mechanism configured to direct a flow of the bodily-fluid. For example, FIGS. 11-15 illustrate a syringe-based transfer device 400 according to an embodiment. The syringe-based transfer device 400 (also referred to herein as "bodily-fluid transfer device," "fluid transfer device," or "transfer device") includes a housing 401, a flow control mechanism 430, and an actuator mechanism 440. Furthermore, the transfer device 400 is configured to include or define a first fluid reservoir 480 (also referred to herein as "first reservoir" or "pre-sample reservoir") and a second fluid reservoir 490 (also referred to herein as "second reservoir" or "sample reservoir"). The transfer device 400 can be any suitable shape, size, or configuration. For example, while shown in FIGS. 11 and 12 as being substantially cylindrical, the transfer device 400 can be square, rectangular, polygonal, and/or any other non-cylindrical shape. Moreover, portions of the transfer device 400 can be substantially similar to the corresponding portions of the transfer device 200, described above in reference to FIGS. 2-6. Therefore, such portions are not described in further detail herein and should be considered substantially similar unless explicitly described differently.

Figure 11:
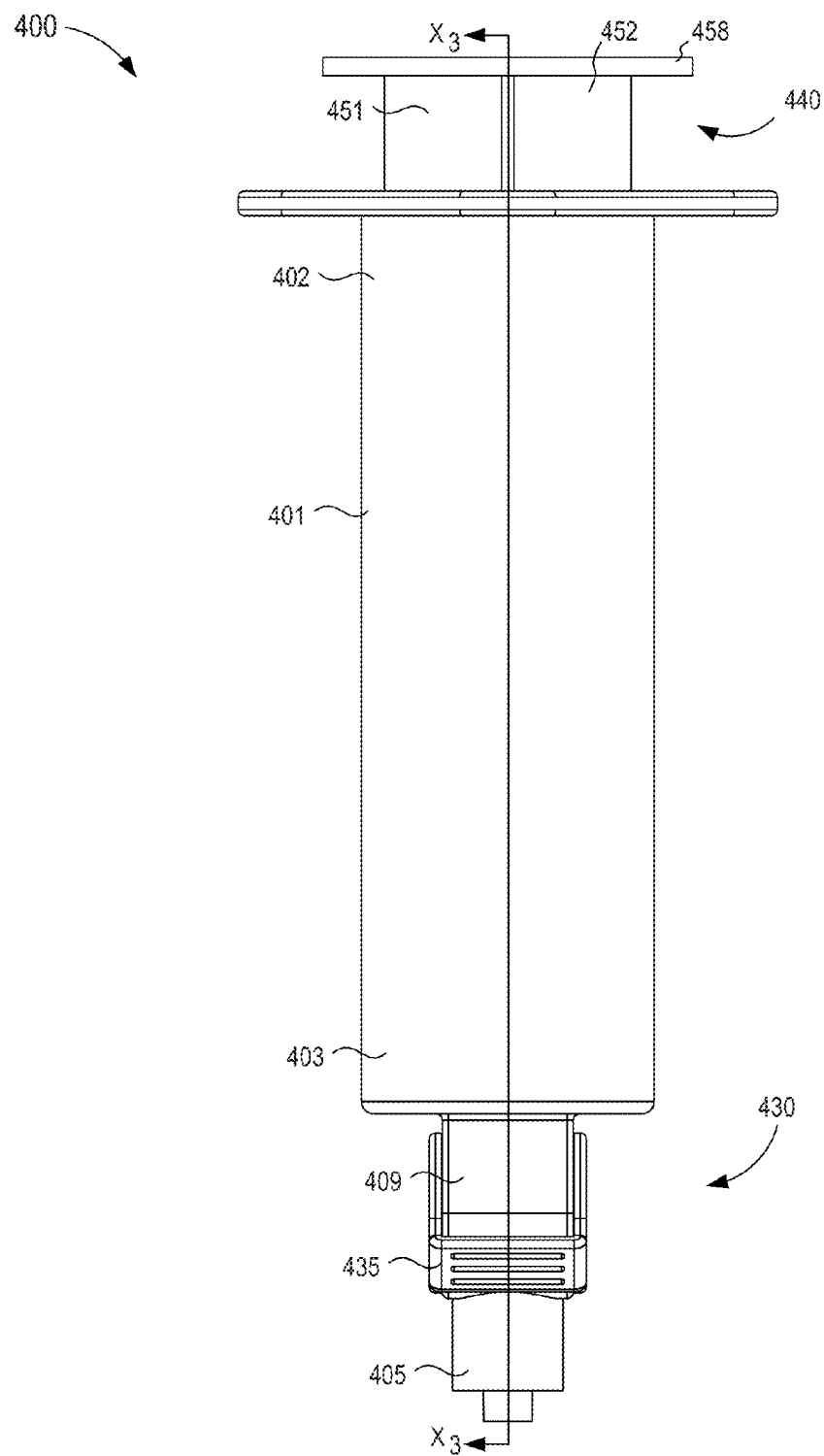
FIG. 11 is a front view of a syringe-based transfer device according to an embodiment, in a first configuration.
Figure 12:
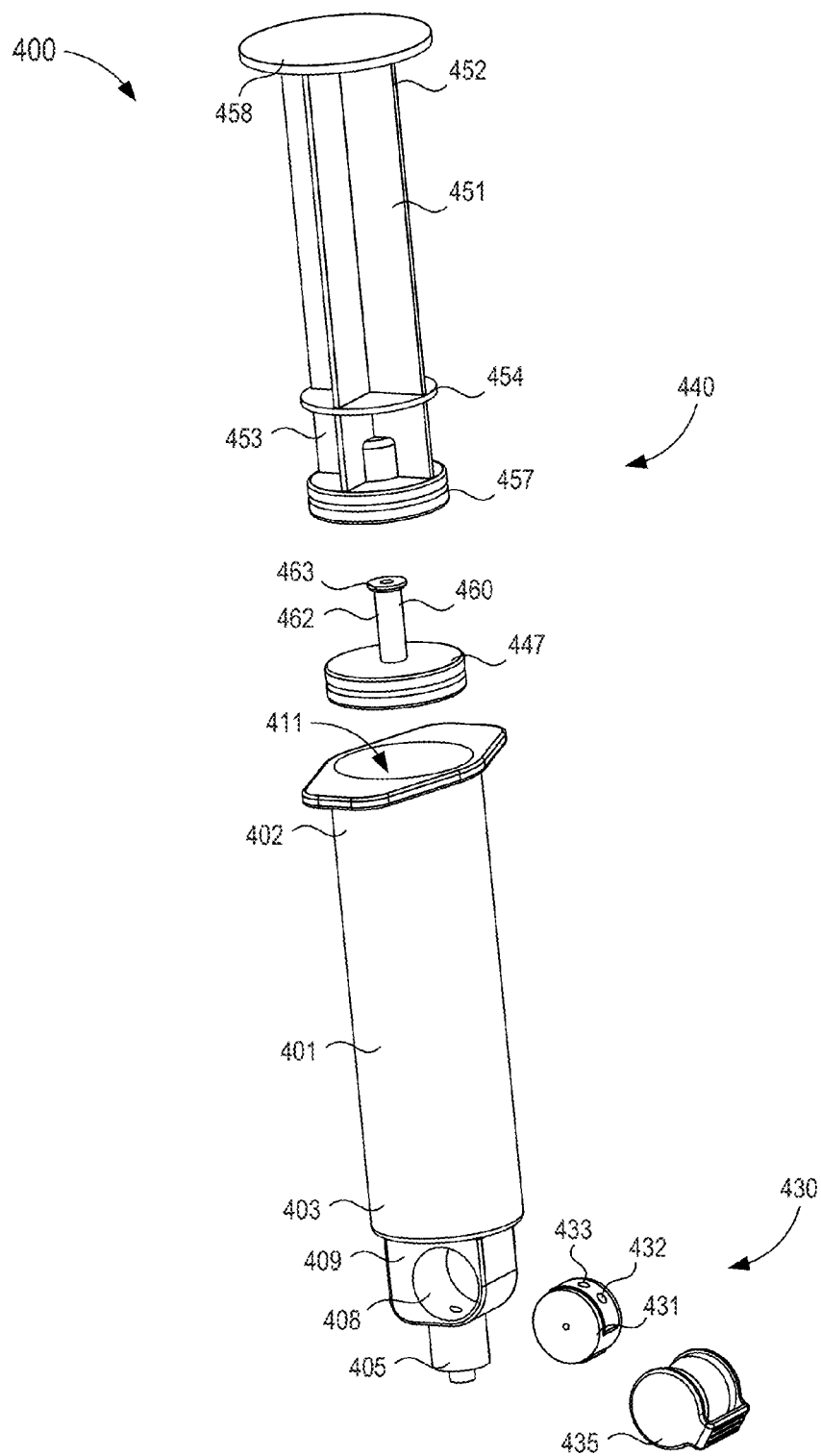
FIG. 12 is an exploded view of the syringe-based transfer device of FIG. 11.

As shown in FIGS. 11 and 12, the housing 401 includes a proximal end portion 402, a distal end portion 403, and defines an inner volume 411 therebetween. The proximal end portion 402 of the housing 401 is substantially open and is configured to receive at least a portion of the actuator mechanism 440 such that the portion of the actuator mechanism 440 is movably disposed within the inner volume 411. Furthermore, the inner volume 411 is configured to define, at least partially, the first fluid reservoir 480 the second fluid reservoir 490, as further described herein.

Figure 13:
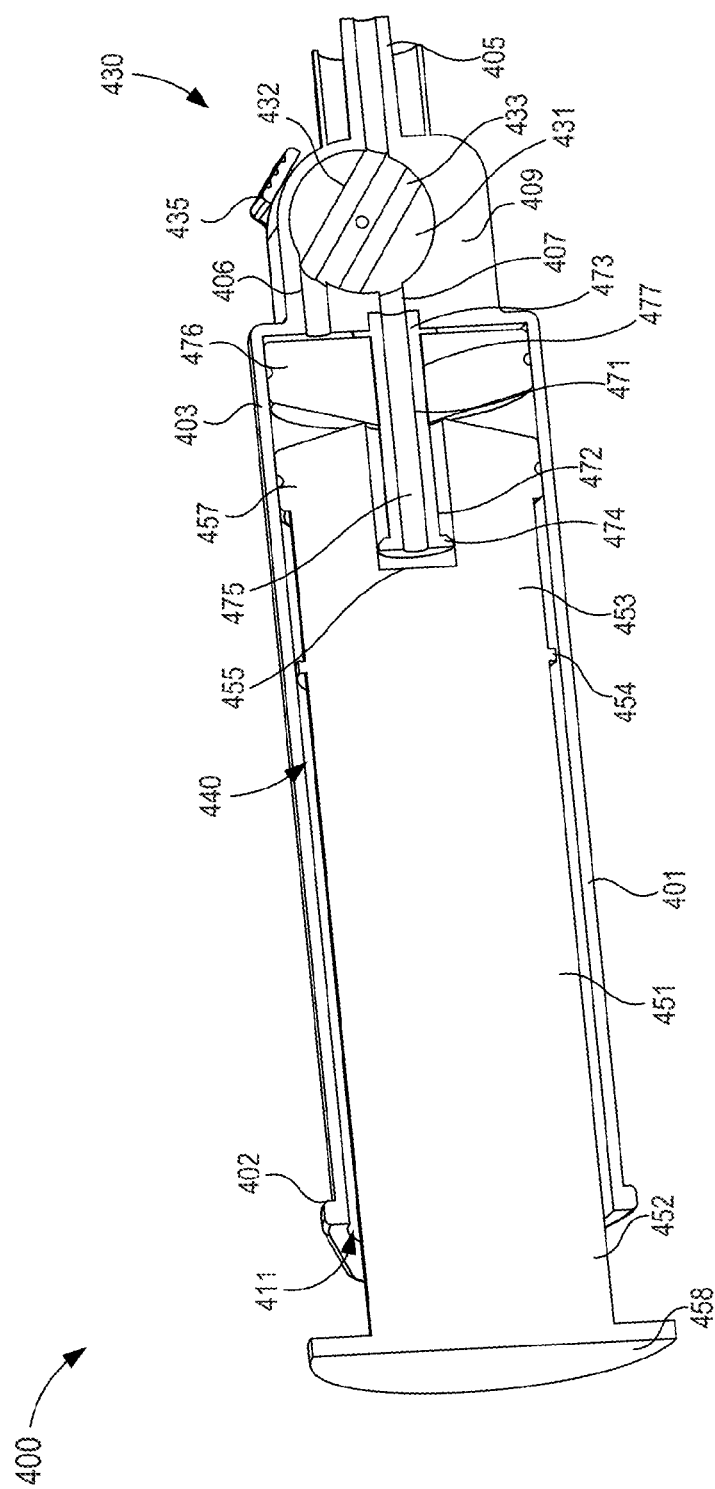
FIG. 13 is a cross-sectional view of the syringe-based transfer device of FIG. 11 taken along the line $X_3$-$X_3$, in the first configuration.

The distal end portion 403 of the housing 401 includes a port 405 and a diverter 409. The port 405 is configured to be coupled to or monolithically formed with a lumen-containing device, such as those described above. The diverter 409 defines a void 408 that movably receives a portion of the flow control mechanism 430. As shown in FIG. 13, the void 408 is in fluid communication with the port 405. The diverter 409 further defines a first lumen 406 in fluid communication with the void 408 and a first portion of the inner volume 411, and a second lumen 407 in fluid communication with the void 408 and a second portion of the inner volume 411. In this manner, the diverter 409 can selectively receive a flow of a bodily-fluid as further described herein.

Referring back to FIG. 12, the flow control mechanism 430 includes a first member 431 and a second member 435. As described above, at least a portion of the flow control mechanism 430 is movably disposed within a portion of the housing 401. More specifically the first member 431 is rotatably disposed within the void 408 of the diverter 409. The first member 431 defines a first lumen 432 and a second lumen 433 and defines a circular cross-sectional shape. In this manner, the first member 431 can be disposed within the void 408 such that a portion of the first member 431 forms a friction fit with the walls of the diverter 409 defining the void 408. For example, in some embodiments, the first member 431 is formed from silicone and has a diameter larger than the diameter of the void 408. In this manner, the diameter of the first member 431 is reduced when the first member 431 is disposed within the void 408. Thus, the outer surface of the first member 431 forms a friction fit with the inner surface of the walls defining the void 408. In other embodiments, the first member 431 can be any suitable elastomer configured to deform when disposed within the void 408 of the diverter 409.

The second member 435 is disposed substantially outside the void 408 and can be engaged by a user to rotate the flow control mechanism 430 between a first configuration and a second configuration. In addition, the first member 431 can be coupled to and/or otherwise engage the second member 445. For example, in some embodiments, the second member 435 can be coupled to the first member 431 via a mechanical fastener and/or adhesive. In other embodiments, the second member 435 and the first member 431 can be coupled in any suitable manner. Therefore, the first member 431 is configured to move concurrently with the second member 435 when the second member 435 is rotated relative to the housing 401. In this manner, the flow control mechanism 430 can be rotated to place the first lumen 432 or the second lumen 433 in fluid communication with the port 405, the first lumen 406, and/or the second lumen 407, as described in further detail herein.

As described above, the actuator mechanism 440 is disposed within the inner volume 411 and is movable between a first position (e.g., a distal position relative to the housing 401) and a second position (e.g., a proximal position relative to the housing 401). Furthermore, the movement of the actuator mechanism 440 relative to the housing 401 can move the transfer device 400 between a first, second, and third configuration, as further described herein. The actuator mechanism 440 includes a first member 4701 and a second member 451. The first member 470 includes a shunt tube 471 and a plunger 476. The plunger 476 defines a channel 477 is configured to be movably disposed about the shunt tube 471. Similarly stated, the shunt tube 471 is disposed within the channel 477. The plunger 476 can be substantially similar in function to those described in detail above. For example, the plunger 476 can be configured to form a friction fit with a set of walls that define the inner volume 411 of the housing 401. In this manner, the plunger 476 and the walls defining the inner volume 411 form a substantially fluid tight seal. Similarly, the plunger 476 and the shunt tube 471 form a substantially fluid tight seal. Therefore, the plunger 476 fluidically isolates a portion of the inner volume 411 proximal of the plunger 476 from a portion of the inner volume 411 distal of the plunger 476.

The shunt tube 471 includes a proximal end portion 472 and a distal end portion 473. The distal end portion 473 is coupled to a portion of the diverter 409 such that a lumen 475 defined by the shunt tube 471 is in fluid communication with the second lumen 407 defined by the diverter 409. The proximal end portion 472 of the shunt tube 471 includes a protrusion 474 that is configured to engage the plunger 476 to substantially limit a proximal movement of the plunger 476 relative to the shunt tube 471, as further described herein.

The second member 451 of the actuator mechanism 440 includes a proximal end portion 452 and a distal end portion 453. The proximal end portion 452 includes an engagement portion 458 that can be engaged by a user (e.g., a phlebotomist, a nurse, a technician, a physician, etc.) to move at least a portion of the actuator mechanism 440 relative to the housing 401. The distal end portion 453 includes a plunger 457 configured to form a friction fit with the inner surface of the walls defining the inner volume 446 when the second member 451 is disposed with the inner volume 411. Similarly stated, the plunger 457 defines a fluidic seal with the inner surface of the walls defining the inner volume 411 such that a portion of the inner volume 411 proximal of the plunger 457 is fluidically isolated from a portion of the inner volume 411 distal of the plunger 457.

While not shown in FIGS. 11-15, the second member 451 can be at least temporarily coupled to the plunger 476 of the first member 470. For example, in some embodiments, the plunger 457 of the second member 451 can include a protrusion configured to be disposed within a groove defined by the plunger 476 of the first member 470. In this manner, the first member 470 and the second member 451 can be configured to collectively move, at least temporarily, within the housing 401, and can further be configured to move, at least temporarily, relative to each other.

As shown in FIG. 13, the distal end portion 453 defines a channel 459 configured to be selectively disposed about a portion of the shunt tube 471. Expanding further, the channel 459 can be configured to have a diameter that is sufficiently large such that the second member 451 can freely move about the shunt tube 471 (e.g., the shunt tube 471 and the walls defining the channel do not form a substantial friction fit.

In use, a user can engage the transfer device 400 to couple the port 405 to a proximal end portion of a lumen-defining device (not shown) such as, for example, a butterfly needle, a cannula assembly, a trocar (which in some cases is used to insert a catheter into a patient), or the like. With the port 405 physically coupled to the lumen-defining device, the port 405 is placed in fluid communication with the lumen defined by the lumen-defining device. Furthermore, the distal end portion of the lumen-defining device can be disposed within a portion of the body of a patient (e.g., a vein, spinal column, etc.). In this manner, the port 405 is placed in fluid communication with the portion of the body.

With the port 405 coupled to the lumen-defining device, a user (e.g., a phlebotomist, a nurse, a technician, a physician, or the like) can move the transfer device 400 from the first configuration to the second configuration. More specifically, the user can engage the engagement portion 458 of the second member 451 included in the actuator mechanism 440 to move the actuator mechanism 440 from its first configuration to its second configuration, thereby placing the transfer device 400 in the second configuration, as indicated by the arrow II in FIG. 14. In this manner, the actuator mechanism 440 is moved in a proximal direction relative to the housing 401

Figure 14:
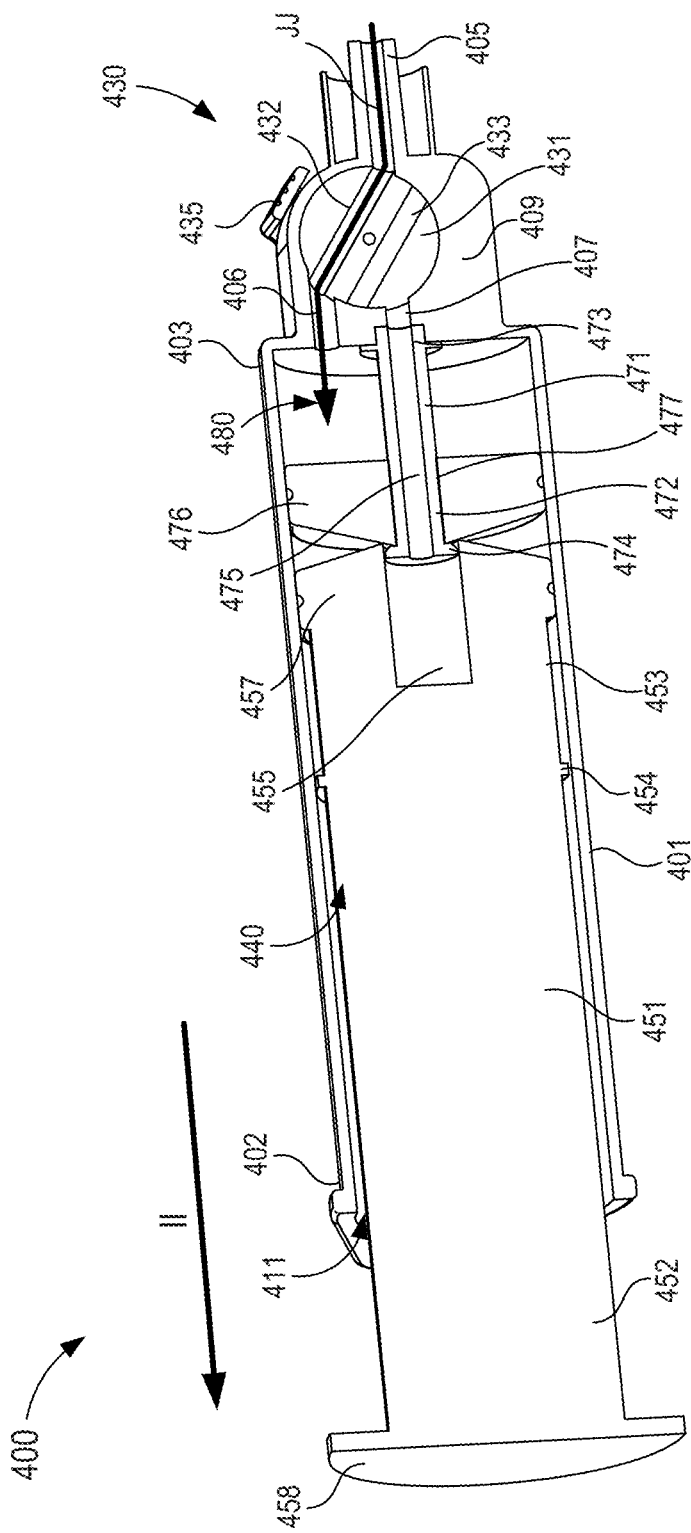
FIG. 14 is a cross-sectional view of the syringe-based transfer device of FIG. 11 taken along the line $X_3$-$X_3$, in a second configuration.

The arrangement of the actuator mechanism 440 is such that the proximal motion of the second member 451 moves the plunger 476 of the first member 470 in the proximal direction relative to the shunt tube 471. Expanding further, the first member 470 can be at least temporarily coupled to the second member 451 such that the first member 470 and the second member 451 move concurrently in the proximal direction relative to the housing 401. In this manner, the first member 470 moves in the proximal direction until the first member 470 is placed in contact with the protrusion 474 included in the shunt tube 471. Moreover, the proximal movement of the plunger 476 increases the volume of the portion of the inner volume 411 of the housing 401 that is distal of the plunger 476, thereby defining the first reservoir 480, as shown in FIG. 14. With the plunger 476 forming a fluid tight seal with the inner surface of the walls defining the inner volume 411 and with the shunt tube 471 about which the plunger 476 is disposed, the volume increase of the portion of the inner volume 411 can produce a negative pressure within the first reservoir 480.

While the transfer device 400 is placed in the second configuration, the flow control mechanism 430 can be maintained in the first configuration. In this manner, first member 431 of the flow control mechanism 430 can be disposed within the void 408 such that the first lumen 432 defined by the flow control mechanism 430 is in fluid communication with the port 405 and in fluid communication with the first lumen 406 defined by the diverter 409. In this manner, the port 405, the first lumen 432 defined by the flow control mechanism 430, and the first lumen 406 defined by the diverter 409 define a fluid flow path that places the first reservoir 480 in fluid communication with the lumen-defining device, as indicated by the arrow JJ in FIG. 14. Therefore, the first reservoir 480 is placed in fluid communication with the portion of the patient (e.g., the vein). Expanding further, the negative pressure within the first reservoir 480 produced by the movement of the plunger 476 (as indicated by the arrow II) introduces a suction force within the portion of the patient. Thus, a bodily-fluid is drawn through the port 405, the first lumen 432 defined by the flow control mechanism 430, and the first lumen 406 defined by the diverter 409 and into the fluid reservoir 480. In some embodiments, the bodily-fluid can contain undesirable microbes such as, for example, dermally-residing microbes and/or other external contaminants.

In some embodiments, the magnitude of the suction force can be modulated by moving the rotating the flow control mechanism 430 relative to the diverter 409. The rotation of the flow control mechanism 330 reduces the size of the fluid pathway (e.g., an inner diameter) between the port 405 and the first lumen 432 of the flow control mechanism 430 and the first lumen 406 of the diverter 409 and the first lumen 432 of the flow control mechanism 430, thereby reducing the suction force introduced into the vein of the patient.

With the desired amount of bodily-fluid transferred to the first reservoir 480, a user can engage the transfer device 400 to move the transfer device 400 from the second configuration to the third configuration. In some embodiments, the desired amount of bodily-fluid transferred to the first reservoir 480 is a predetermined amount of fluid (as described above). In some embodiments, the volume of the first reservoir 480 is sufficient to contain the first centiliter or few centiliters of bodily-fluid. In other embodiments, the first reservoir 480 can be configured to contain from about 0.1 ml to about 3.0 ml. In still other embodiments, the first reservoir 480 can be configured to contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. In some embodiments, the predetermined amount of bodily-fluid (e.g., volume) is at least equal to the combined volume of the port 405, the first lumen 432 of the flow control mechanism 430, the first lumen 406 of the diverter 409, and the lumen-defining device. In other embodiments, the flow control mechanism 430 can be configured to automatically move from the first configuration to the second configuration to divert fluid flow without user intervention.

Figure 15:
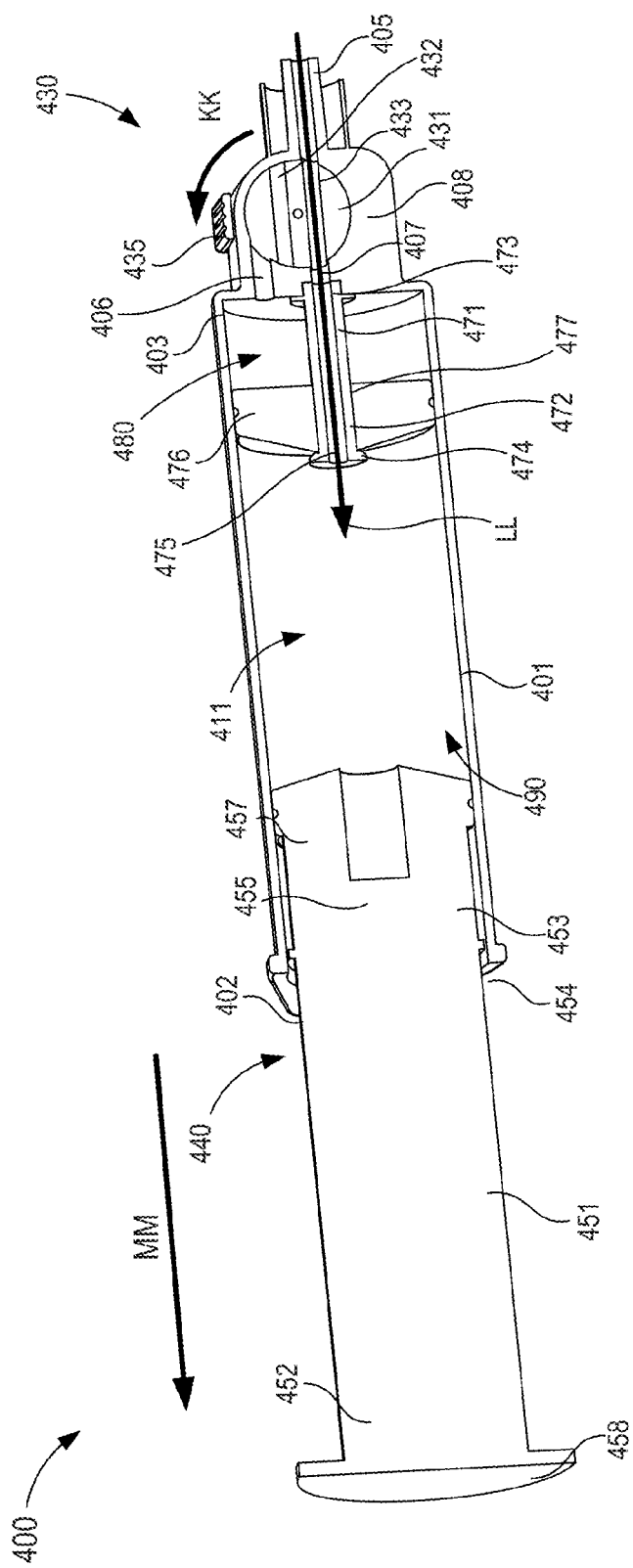
FIG. 15 is a cross-sectional view of the syringe-based transfer device of FIG. 11 taken along the line $X_3$-$X_3$, in a third configuration.

As shown in FIG. 15, the transfer device 400 can be moved from the second configuration to the third configuration by rotating the second member 435 of the flow control mechanism 430 relative to the diverter 409, as indicated by the arrow KK. In this manner, the flow control mechanism 430 is moved to the second configuration, and the first lumen 432 is fluidically isolated from the port 405 and the first lumen 406 of the diverter 409. Thus, the first reservoir 480 is fluidically isolated from a volume substantially outside the first reservoir 480. In addition, the second lumen 433 defined by the flow control mechanism 430 is placed in fluid communication with the port 405 and the second lumen 407 defined by the diverter 409. Therefore, the port 405, the second lumen 433 of the flow control mechanism 430, the second lumen 407 of the diverter 409, and the lumen 475 of the shunt tube 471 define a fluid flow path, as indicated by the arrow LL.

With the flow control mechanism 430 placed in the second configuration, the second member 451 of the actuator mechanism 440 can be moved from the second configuration to a third configuration. Expanding further, with the plunger 476 in contact with the protrusion 474 of the shunt 471, the second member 451 can be moved in the proximal direction to decouple the second member 451 from the plunger 476 (as described above the plunger 476 is at least temporarily coupled to the first member 451). In this manner, the second member 451 can be moved in the proximal direction relative to the first member 470, as indicated by the arrow MM in FIG. 15. The proximal movement of the second member 451 relative to the first member 470 increases the volume of the portion of the inner volume 411 that is proximal of the plunger 476 of the first member 470 and distal of the plunger 457 of the second member 451, thereby defining the second reservoir 490.

With the plunger 476 of the first member 470 and the plunger 457 of the second member 451 forming a fluid tight seal with the inner surface of the walls defining the inner volume 411, the volume increase of the portion of the inner volume 411 can produce a negative pressure within the first reservoir 490. Thus, the negative pressure within the second reservoir 490 is such that the negative pressure differential between the second reservoir 490 and the portion of the body of the patient introduces a suction force within the portion of the patient. Therefore, a desired amount of bodily-fluid is drawn through the port 405, the second lumen 433 of the flow control mechanism 430, the second lumen 407 of the diverter 409, and the lumen 475 defined by the shunt tube 471 and into the second reservoir 490. Moreover, the bodily-fluid disposed within the second reservoir 490 is fluidically isolated from the first, predetermined amount of bodily-fluid contained within the first reservoir 480.

Although not shown in FIGS. 11-15, in some embodiments, the syringe-based transfer device 400 can be coupled to a device in fluid communication with the patient that is also configured to reduce contamination of a patient sample. For example, in some embodiments, the syringe-based transfer device 400 can be used with a lumenless needle or the like such as those described in the '758 application.

While not shown in FIGS. 11-15, the actuator mechanism 440 can be moved from the third configuration to a fourth configuration to place the transfer device 400 in a fourth configuration. For example, in some embodiments, with the desired amount of bodily-fluid disposed within the second fluid reservoir 490, the transfer device 400 can be removed from the portion of the patient and disposed above or in a container (e.g., a vile, a test tube, a petri dish, a culture medium, a test apparatus, or the like) such that a portion of the second amount of bodily-fluid can be tested. Expanding further, the user can apply a force to the engagement portion 458 to move the second member 451 in the distal direction. Therefore, the force applied to the engagement portion 458 moves the second member 451 in the distal direction relative to the housing 301 to expel a desired portion of the second amount of bodily-fluid from the lumen-defining device and into the container.

While the transfer device 400 is shown and described above as including the flow control mechanism 430 that defines the first lumen 432 and the second lumen 433 that selectively place the port 405 in fluid communication with the first reservoir 480 and the second reservoir 490, respectively, in other embodiments, a transfer device can include a flow control mechanism with one or more portions configured to selectively block or obstruct flow of a bodily-fluid. For example, FIGS. 16 and 17 illustrate at least a portion of a syringe-based transfer device 500 according to an embodiment. The syringe-based transfer device 500 (also referred to herein as "bodily-fluid transfer device," "fluid transfer device," or "transfer device") includes a housing 501 and a flow control mechanism 530, and defines a fluid reservoir 580 (also referred to herein as "first reservoir" or "pre-sample reservoir"). Although not shown in FIGS. 16 and 17, the transfer device 500 can be coupled to and/or include an actuator or the like. For example, in some embodiments, the housing 501 can include a proximal port 515 that can be coupled to a syringe or the like. In such embodiments, the proximal port 515 can be physically and fluidically coupled to, for example, a distal port of the syringe. In some embodiments, the syringe can be configured to define a fluid reservoir (e.g., a sample reservoir not shown FIGS. 16 and 17) that can receive a flow of bodily-fluid. In other embodiments, the proximal port 515 can be configured to receive an actuator that includes a plunger. In such embodiments, the plunger can form a substantially fluid tight seal with an inner surface of the proximal port 515, thereby fluidically isolating a first volume that is proximal to the plunger from a second volume that is distal to the plunger. In still other embodiments, the proximal port 515 can be physically and fluidically coupled to a fluid reservoir that can, for example, define a negative pressure. In this manner, the proximal port 515 of the housing 501 can be coupled to any suitable device, mechanism, assembly, subassembly, or the like that can introduce a negative pressure within at least a portion of the housing 501 and/or that can define a fluid reservoir configured to receive a flow of bodily-fluid, as described in further detail herein.

As shown in FIGS. 16 and 17, the housing 501 includes a distal port 505 and a diverter 509, and defines an inner volume 511 that is in fluid communication with the distal port 505 and the proximal port 515. The inner volume 511 can define, at least partially, the fluid reservoir 580, as further described herein. The diverter 509 can be any suitable configuration. For example, in some embodiments, the diverter 509 can be a set of walls that can extend into the inner volume 511 to direct a fluid of bodily-fluid within the inner volume 511. For example, as shown in FIGS. 16 and 17, the diverter 509 can be an annular wall or set of annular walls that can circumscribe a portion of the inner volume 511. Moreover, the arrangement of the diverter 509 within the inner volume 511 can be such that the diverter 509 and a set of wall of the housing 501 defining the inner volume 511 define, at least partially, a first channel 506 and a second channel 507 that can be selectively placed in fluid communication with the proximal port 515 and the distal port 505, as described in further detail herein. The diverter 509 also includes a wall or set of walls that can form a substantially wedge-shaped portion 510 of the diverter 509. For example, as shown in FIGS. 16 and 17, the walls of the diverter 509 forming the wedge-shaped portion 510 can extend in a radial direction from a center of the inner volume 511. In this manner, the wedge-shaped portion 510 can divide and/or obstruct a portion of the inner volume 511 to define at least a portion of the fluid reservoir 580. Moreover, the wedge-shaped portion 510 can define a channel 516 or flow path that can be selectively obstructed by a portion of the flow control mechanism 530 to, for example, fluidically isolate the fluid reservoir 580 from the proximal port 515, as described in further detail herein.

The flow control mechanism 530 of the transfer device 500 includes a first member 537, a second member 538, and a third member 539. At least a portion of the flow control mechanism 530 is movably disposed within a portion of the inner volume 511 of the housing 501. More specifically, the first member 537 is rotatably coupled to a hub 517 of the housing 501 disposed within the void 508 of the diverter 509. Similarly, the second member 538 and the third member 539 can be rotatably coupled to an outer surface of the annular wall defining a portion of the diverter 509 and a peripheral portion of the housing 501 defining the inner volume 511, respectively. The first member 537, the second member 538, and the third member 539 can be any suitable shape, size, or configuration. For example, in some embodiments, the first member 537, the second member 538, and the third member 539 can be valves or the like that can be arranged in a gate configuration or the like. More specifically, the first member 537, the second member 538, and the third member 539 can be substantially thin elongate members that can be selectively placed in contact with an inner surface of the housing 501. For example, the first member 537 can extend in a radial direction from the hub 517 to be placed in contact with an inner surface of the annular wall forming at least a portion of the diverter 509. Furthermore, the first member 537 can be formed from a relatively flexible and/or compressible material such that the first member 537 forms a substantially fluid tight seal with the inner surface of the annular wall. In this manner, the first member 537 and the wedge-shape portion 510 of the diverter 509 can collectively define at least a portion of the fluid reservoir 580 therebetween and the first member 537 can fluidically isolate the fluid reservoir 580 from, for example, a portion of the inner volume 511 in fluid communication with the proximal port 515, as described in further detail herein.

The second member 538 and the third member 539 of the flow control mechanism can be arranged in a similar manner. For example, the second member 538 can extend from an outer surface of the annular wall forming a portion of the diverter 509 to be placed in contact with the inner surface of the housing 511. In use, the second member 538 can be rotated between a first position and a second position to selectively place the first channel 506 and the second channel 507, respectively, in fluid communication with the distal port 505. Similarly, the third member 539 can extend from the inner surface of a peripheral wall of the housing 501 defining the inner volume 511 to be placed in contact with the outer surface of the annular wall forming a portion of the diverter 509. In use, the third member can be rotated between a first position and a second position to selective place the distal port 505 in fluid communication with the proximal port 515.

In use, a phlebotomist, technician, physician, nurse, etc., can manipulate the transfer device 500 by physically and fluidically coupling the proximal port 515 to a syringe or the like (not shown in FIGS. 16 and 17). In some embodiments, the syringe can form a sample reservoir or the like configured to receive a flow of bodily-fluid that is substantially free from, for example, dermally residing microbes. As shown in FIG. 16, the first member 537, the second member 538, and the third member 539 can each be in their first position relative to the housing 501 such that the first channel 506 is in fluid communication with the distal port 505, while the second channel 507 is fluidically isolated from the distal port 505 and the proximal port 515. Although not shown in FIGS. 16 and 17, the distal port 505 can be coupled to a proximal end portion of a lumen-defining device such as, for example, a butterfly needle, a cannula assembly, a trocar (which in some cases is used to insert a catheter into a patient), or the like. With the port 505 physically coupled to the lumen-defining device, the port 505 is placed in fluid communication with the lumen defined by the lumen-defining device. Furthermore, the distal end portion of the lumen-defining device can be disposed within a portion of the body of a patient (e.g., a vein, spinal column, etc.). In this manner, the port 505 is placed in fluid communication with the portion of the body. While described above as physically and fluidically coupling the proximal port 515 to the syringe prior to coupling the distal port 505 to the lumen-defining device, in some instances, the distal port 505 can be coupled to the lumen-defining device prior to coupling the proximal port 515 to the syringe.

With the port 505 coupled to the lumen-defining device, a user (e.g., the phlebotomist, the technician, the physician, the nurse, etc.) can move the transfer device 500 from a first configuration to a second configuration. More specifically, the user can manipulate the transfer device 500 to rotate the first member 537 relative to the housing 501 from its first position to its second position relative to the housing 501, as indicated by the arrow NN in FIG. 16. In some instances, the proximal port 515 can be coupled to a syringe based device or the like that can, for example, introduce a negative pressure in a portion of the inner volume 511 that exerts a suction force through the channel 516, which, in turn, is operable in rotating the first member 537 from its first position to its second position. Similarly stated, the negative pressure produced by the syringe can exert a suction force through the channel 516 to rotate the first member 537 from its first position to its second position without direct manual intervention from the user on the first member 537. With the first member 537 forming a substantially fluid tight seal with the inner surface of the diverter 509 and/or the housing 501, the rotation of the first member 537 increases a volume of the fluid reservoir 580 defined, at least in part, between the wedge-shaped portion 510 of the diverter 509 and the first member 537, which, in turn, produces a negative pressure with the fluid reservoir 580. Moreover, with the first channel 506 in fluid communication with the fluid reservoir 580 and the distal port 505, the negative pressure in the fluid reservoir 580 can exert a suction force through the first channel 506 and the distal port 505 that can urge a flow of bodily-fluid from the patient, through the lumen-defining device (not shown) and the first channel 506, and into the fluid reservoir 580, as indicated by the arrow OO in FIG. 16. In some embodiments, the bodily-fluid can contain undesirable microbes such as, for example, dermally-residing microbes and/or other external contaminants.

With the desired amount of bodily-fluid transferred to the first reservoir 580, a user can engage the transfer device 500 to move the transfer device 500 from the second configuration to the third configuration. In some embodiment, the desired amount of bodily-fluid transferred to the first reservoir 580 is a predetermined amount of fluid (as described above). In some embodiments, the volume of the first reservoir 580 is sufficient to contain the first centiliter or few centiliters of bodily-fluid. In other embodiments, the first reservoir 580 can be configured to contain from about 0.1 ml to about 3.0 ml. In still other embodiments, the first reservoir 580 can be configured to contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. In some embodiments, the predetermined amount of bodily-fluid (e.g., volume) is at least equal to the combined volume of the port 505, the first channel 506, and the lumen-defining device. In some embodiments, the first member 537 can be rotated to the second position to place the first member 537 in contact with a portion of wedge-shape portion 510 of the diverter 509 such that the channel 516 is substantially obstructed (see e.g., FIG. 17). Thus, the predetermined volume can be associated with an amount of rotation of the first member 537 and/or a size, shape, angle, etc. of the wedge-shaped portion 510 of the diverter 509.

As shown in FIG. 17, the transfer device 500 can be moved from the second configuration to the third configuration by rotating the second member 538 and the third member 539 of the flow control mechanism 530 relative to the diverter 509 and/or the housing 501, as indicated in FIG. 17 by the arrows PP and QQ, respectively. In this manner, with the first member 537, the second member 538, and the third member 539 rotated to their second positions, the fluid reservoir 580 and the first channel 506 are fluidically isolated from the distal port 505 and the proximal port 515 to sequester the predetermined volume of bodily-fluid in the fluid reservoir 580. In addition, the second channel 507 is placed in fluid communication with the distal port 505 and the proximal port 515, thereby placing the distal port 505 in fluid communication with the syringe. Thus, the user can manipulate the syringe to exert a suction force through the proximal port 515, the second channel 507, the distal port 505, and the lumen-defining device that can urge a flow of bodily-fluid from the patient to, for example, a sample reservoir defined by the syringe, as indicated by the arrow RR. In some instances, sequestering the predetermined volume in the fluid reservoir 580 can be such that the flow of bodily-fluid from the patient to the sample reservoir defined by the syringe (not shown in FIGS. 16 and 17) is substantially free from contaminants (e.g., dermally-residing microbes or the like), as described above.

FIGS. 18-23 illustrate a syringe-based transfer device 600 according to an embodiment. The syringe-based transfer device 600 (also referred to herein as "bodily-fluid transfer device," "fluid transfer device," or "transfer device") is configured to be moved between a first, second, third, and fourth configuration, as further described herein. The transfer device 600 includes a housing 601 and an actuator mechanism 640. Furthermore, the transfer device 600 is configured to include or define a first fluid reservoir 680 (also referred to herein as "first reservoir" or "pre-sample reservoir") and a second fluid reservoir 690 (also referred to herein as "second reservoir" or "sample reservoir").

Figure 18:
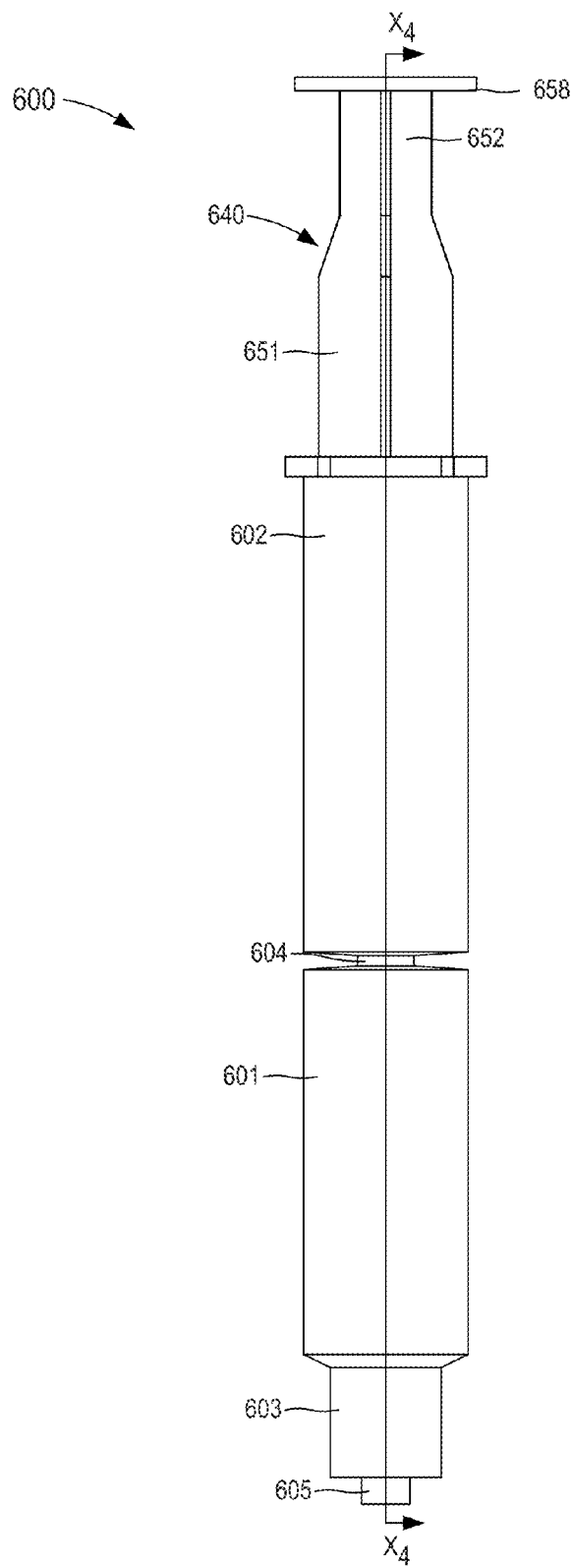
FIG. 18 is a front view of a syringe-based transfer device according to an embodiment, in a first configuration.
Figure 19:
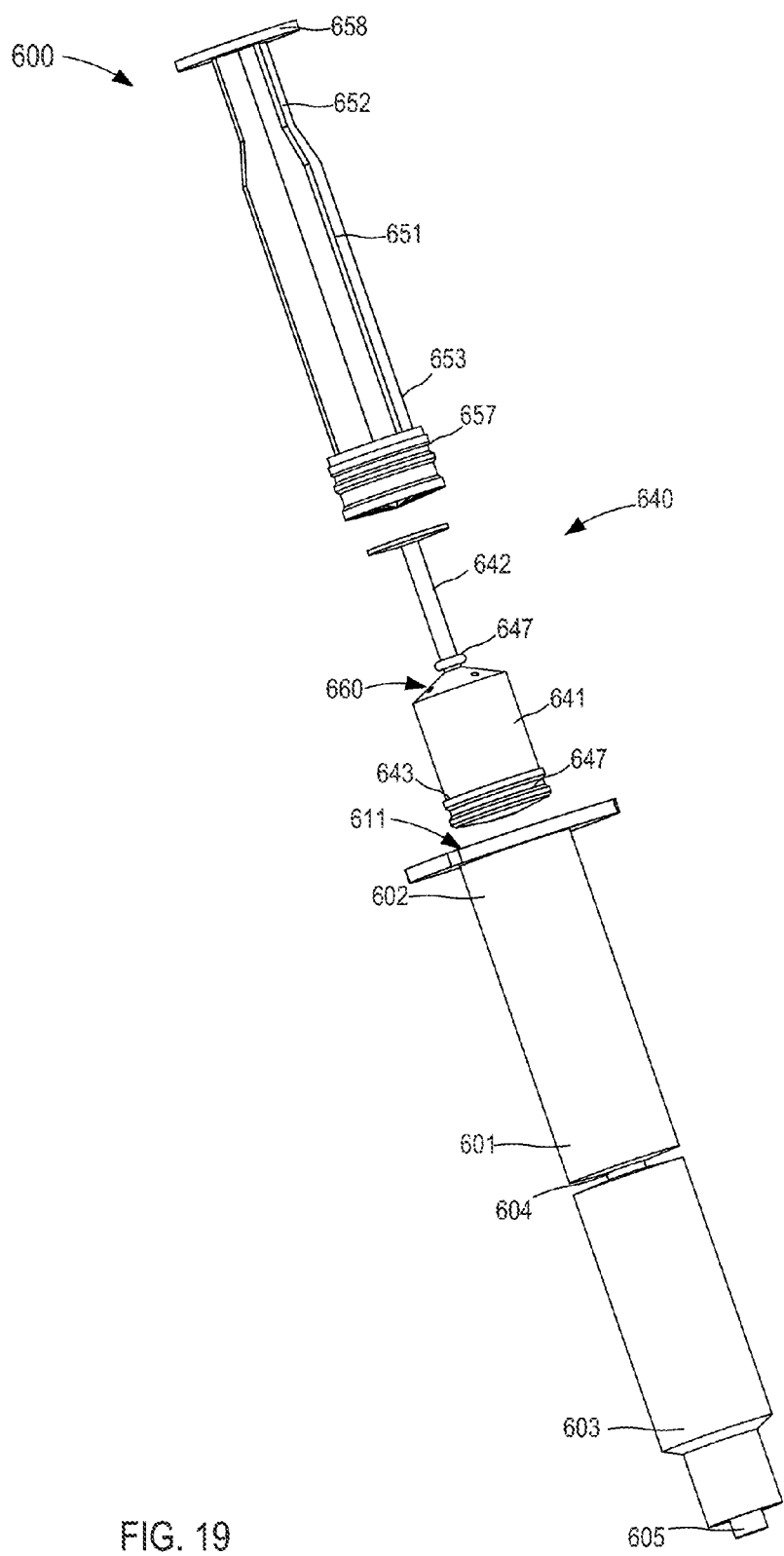
FIG. 19 is an exploded view of the syringe-based transfer device of FIG. 18.
Figure 20:
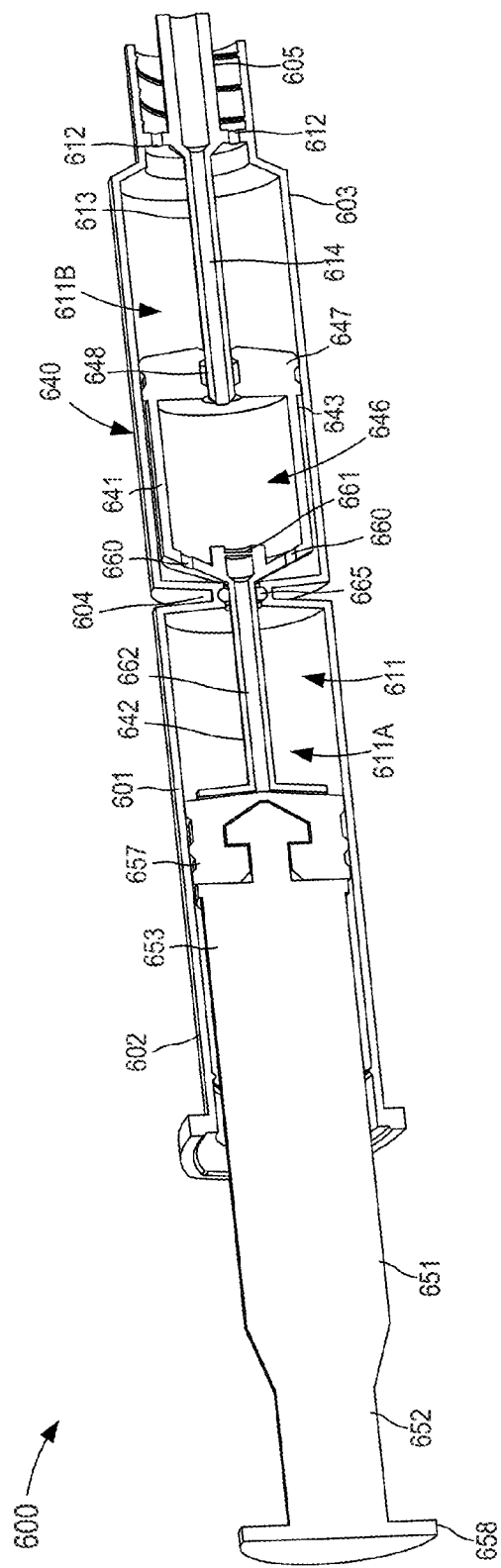
FIG. 20 is a cross-sectional view of the syringe-based transfer device of FIG. 18 taken along the line $X_4$-$X_4$, in the first configuration.
Figure 23:
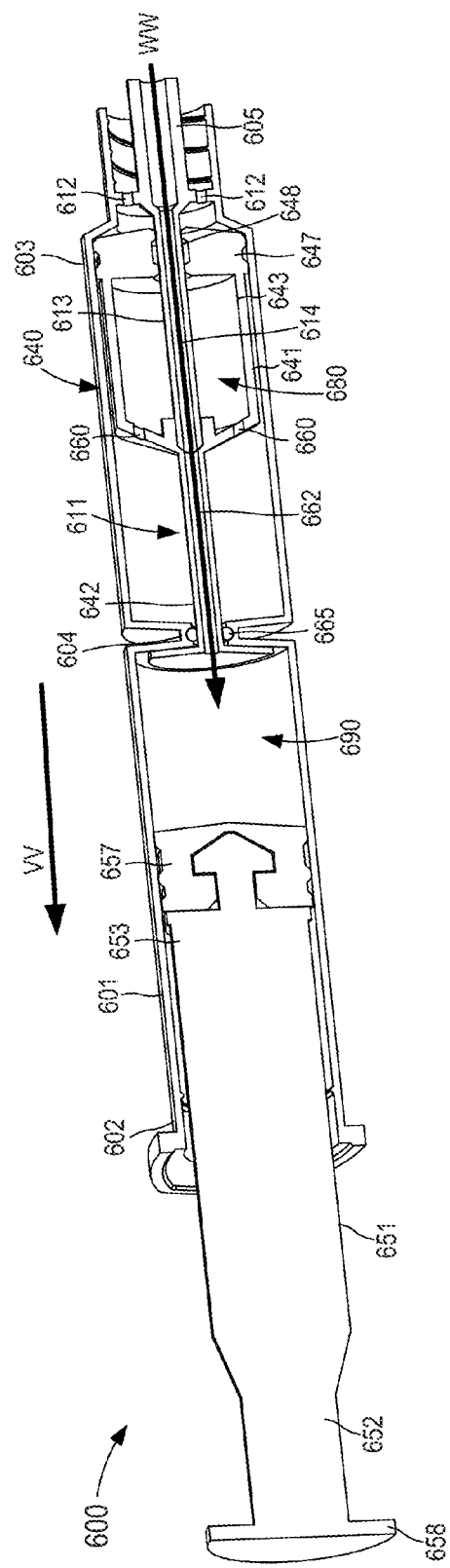
FIG. 23 is a cross-sectional view of the syringe-based transfer device of FIG. 18 taken along the line $X_4$-$X_4$, in a fourth configuration.

As shown in FIGS. 18-20, the housing 601 includes a proximal end portion 602, a distal end portion 603, and a medial portion 604 and defines an inner volume 611. The proximal end portion 602 of the housing 601 is substantially open and is configured to receive at least a portion of the actuator mechanism 640. The distal end portion 603 of the housing 601 includes a port 605, and a set of vents 612. The vents 612 can be configured to allow a gas (e.g., air) to flow from a portion of the inner volume 611 to a volume outside of the housing 601, as described in further detail herein. The port 605 is configured to be coupled to or monolithically formed with a lumen-containing device, such as those described above. Furthermore, as shown in FIG. 20, the port 605 includes an elongate portion 613 that defines lumen 614 and that is configured to extend in a proximal direction from the port to be disposed in a portion of the inner volume 611, as described in further detail herein.

The medial portion 604 of the housing 601 defines and/or forms a substantially constricted portion to the housing 601. For example, the proximal end portion 602 and the distal end portion 603 can have a first diameter that is greater than a second diameter of the medial portion 604. In this manner, the medial portion 604 can form a channel or lumen between a first portion 611A of the inner volume 611 defined by the proximal end portion 602 of the housing 601 and a second portion 611B of the inner volume 611 defined by the distal end portion 603 that can movably receive a portion of the actuator mechanism 640. Moreover, the medial portion 604 can include a seal member 665 such as, for example, an O-ring or the like that can form a substantially fluid tight seal with the portion of the actuator mechanism 640, thereby fluidically isolating the first portion 611A of the inner volume 611 from the second portion 611B of the inner volume 611, as described in further detail herein.

As described above, the actuator mechanism 640 is disposed within the inner volume 611 and is movable between a first position (e.g., a distal position relative to the housing 601) and a second position (e.g., a proximal position relative to the housing 601). Furthermore, the movement of the actuator mechanism 640 relative to the housing 601 can move the transfer device 600 between the first, second, third, and fourth configurations, as further described herein. The actuator mechanism 640 includes a first member 641 and a second member 651. The first member 641 of the actuator mechanism 640 includes a proximal end portion 642 and a distal end portion 643 and defines an inner volume 646. At least a portion of the inner volume 646 is configured to define the first reservoir 680, as further described herein. As shown in FIG. 20, a portion of the first member 641 can be movably disposed in the channel or lumen defined by the medial portion 604 of the housing 601 such that a first portion of the first member 641 is disposed in the first portion 611A of the inner volume 611 and a second portion of the first member 641 is disposed in the second portion 611B of the inner volume 611.

The proximal end portion 642 of the first member 641 forms a substantially elongate member or shunt tube that is configured to extend through the medial portion 604 of the housing 601. In some embodiments, at least a part of the proximal end portion 642 can have a diameter that substantially corresponds with a diameter of the channel or lumen defined by the medial portion 604 of the housing 601. As such, the seal member 665 can form a substantially fluid tight seal with the outer surface of the proximal end portion. Moreover, the proximal end portion 642 defines a lumen 662 that extends through the proximal end portion 642 such that at least a portion of the first member 641 can be placed in fluid communication with the first portion 611A of the inner volume 611, as described in further detail herein.

The distal end portion 643 of the first member 641 is movably disposed in the second portion 611B of the inner volume 611. The distal end portion 643 includes a plunger 647 and a frangible seal 661, and defines a set of vents 660. The vents 660 can be configured to allow a gas (e.g., air) to flow from the first fluid reservoir 680 to the second portion 611B of the inner volume 611, as described in further detail herein. The frangible seal 661 can be configured to selectively fluidically isolate the lumen 662 defined by the proximal end portion 642 from the inner volume 646, as described in further detail herein. The plunger 647 forms a friction fit with the inner surface of the walls defining the second portion 611B of the inner volume 611. The plunger 647 defines a channel 648 that extends though a distal end and a proximal end of the plunger 647. As shown in FIG. 20, the channel 648 can receive the elongate portion 613 of the port 605 and can be arranged to form a substantially fluid tight seal with an outer surface of the elongate member 613. In this manner, the distal end portion 643 can be disposed about the elongate member 613 and moved between a first position (e.g., a proximal position) and a second position (e.g., a distal position) relative to the housing 601, as described in further detail herein.

The second member 651 of the actuator mechanism 640 is movably disposed in the first portion 611A of the inner volume 611 and includes a proximal end portion 652 and a distal end portion 653. The proximal end portion 652 includes an engagement portion 658 that can be engaged by a user (e.g., a phlebotomist, a nurse, a technician, a physician, etc.) to move at least a portion of the actuator mechanism 640 relative to the housing 601. The distal end portion 653 includes a plunger 657 configured to form a friction fit with the inner surface of the walls defining the first portion 611A of the inner volume 611. As described in further detail herein, the second member 651 can be movable within the first portion 611A of the inner volume 611 between a first position (e.g., a distal position) and a second position (e.g., a proximal position).

In use, a user can engage the transfer device 600 to couple the port 605 to a proximal end portion of a lumen-defining device (not shown) such as, for example, a butterfly needle, a cannula assembly, a trocar (which in some cases is used to insert a catheter into a patient), or the like. With the port 605 physically coupled to the lumen-defining device, the port 605 is placed in fluid communication with the lumen defined by the lumen-defining device. Furthermore, the distal end portion of the lumen-defining device can be disposed within a portion of the body of a patient (e.g., a vein). In this manner, the port 605 is placed in fluid communication with the portion of the body.

With the port 605 coupled to the lumen-defining device, a user (e.g., a phlebotomist, a nurse, a technician, a physician, or the like) can move the transfer device 600 from the first configuration (FIG. 20) to the second configuration (FIG. 21). For example, the user can engage the engagement portion 658 of the second member 651 to move the actuator mechanism 640 in a distal direction within the inner volume 611, as indicated by the arrow SS in FIG. 21. More specifically, the arrangement of the actuator mechanism 640 can be such that the proximal end portion 642 of the first member 641 is in contact with a distal surface of the plunger 657 included in the second member 651. Thus, the distal movement of the second member 651 within the first portion 611A of the inner volume 611 can move the proximal end portion 642 of the first member 641 through the channel or lumen defined by the medial portion 604 of the housing 601, thereby moving a portion the first member 641, concurrently, within the second portion 611B of the inner volume 611. The arrangement of the first member 641 within the second portion 611B of the inner volume 611 is such that the distal motion of the first member 651 increases the volume of the second portion 611B of the inner volume 611 that is proximal of the plunger 647, which in turn, produces a negative pressure within the second portion 611B of the inner volume 611 that is proximal of the plunger 647 (as described in detail above). Moreover, with the vents 660 placing the first fluid reservoir 680 in fluid communication with the second portion 611B of the inner volume 611 that is proximal of the plunger 647 and with the lumen 614 defined by the elongate portion 613 of the port 605 in fluid communication with the first fluid reservoir 680, the negative pressure can exert a suction force through the port 605 that can be operable in drawing bodily-fluid from the patient, through the port 605 and the lumen 614 defined by the elongate portion 613 and into the first fluid reservoir 680, as indicated by the arrow TT in FIG. 21. In some embodiments, the bodily-fluid can contain undesirable microbes such as, for example, dermally-residing microbes and/or other external contaminants, as described in detail above.

While in the second configuration, the transfer device 600 can be configured to transfer a desired amount (e.g., a predetermined amount) of bodily-fluid transferred to the first reservoir 680. In some embodiments, the first, predetermined amount can substantially correspond to the size of the first reservoir 680. In other embodiments, the first amount can substantially correspond to an equalization of pressure within the first reservoir 680 and the portion of the patient. Moreover, the first reservoir 680 is fluidically isolated from a volume substantially outside the first reservoir 680. For example, in some embodiments, the vents 660 can be configured to allow a flow of a gas (e.g., air) therethrough while substantially preventing a fluid of fluid (e.g., bodily-fluid) therethrough.

With the first amount of bodily-fluid fluidically isolated, the actuator mechanism 640 can be moved from the second configuration to a third configuration by further moving the actuator mechanism 640 in the distal direction. For example, as indicated by the arrow UU in FIG. 22, the user can apply a force to the engagement portion 658 of the second member 651 to move the actuator mechanism 640 relative to the housing 601. Thus, the distal movement of the second member 651 within the first portion 611A of the inner volume 611 moves the proximal end portion 642 of the first member 641 through the channel or lumen defined by the medial portion 604 of the housing 601, thereby moving a portion the first member 641, concurrently, within the second portion 611B of the inner volume 611, as described above. The distal movement of the first member 641 in the second portion 611B of the inner volume 611 can be such that the elongate portion 613 of the port 605 is placed in contact with the frangible seal 661 included in the first member 641. Thus, further distal movement of the first member 641 relative to the elongate portion 613 results in the elongate portion 613 puncturing and/or breaking the frangible seal, as shown in FIG. 22. As such, the lumen 614 defined by the elongate portion 613 of the port 605 can be placed in fluid communication with the lumen 662 of the proximal end portion 642 of the first member 641.

With the lumen 614 of the elongate portion 613 in fluid communication with the lumen 662 of the proximal end portion 642, the user can manipulate the actuator mechanism 640 to move the actuator mechanism 640 from the third configuration to a fourth configuration, thereby placing the transfer device 600 in the fourth configuration. For example, as indicated by the arrow VV in FIG. 23, the user can manipulate the engagement portion 658 to move the second member 651 in a proximal direction relative to the housing 601 and/or the first member 641. Thus, the proximal movement of the second member 651 is such that a volume of the first portion 611A of the inner volume 611 that is distal of the plunger 657 is increased, thereby defining and/or forming the second reservoir 690. Thus, the proximal movement of the second member 651 increases the volume of the second reservoir 690 which produces a negative pressure within the second reservoir 690. Moreover, with the lumen 662 of the proximal end portion 642 of the first member 641 in fluid communication with the first portion 611A of the inner volume 611 and with the lumen 614 of the elongate portion 613 of the port 605 in fluid communication with the lumen 662, the negative pressure exerts a suction force that is operably in drawing a bodily-fluid from the patient, through the lumens 614 and 662 defined by the elongate portion 613 and the proximal end portion 642, respectively, and into the second reservoir 690. In addition, the bodily-fluid contained within the second reservoir 690 is substantially free from microbes generally found outside of the portion of the patient (e.g., dermally residing microbes, microbes within a lumen defined by the transfer device 600, microbes within the lumen defined by the lumen defining device, and/or any other undesirable microbe).

While not shown in FIGS. 18-23, the actuator mechanism 640 can be moved from the fourth configuration to the third configuration once a desired amount of bodily-fluid has been transferred to the second reservoir 690. For example, in some embodiments, with the desired amount of bodily-fluid disposed within the second fluid reservoir 690, the transfer device 600 can be removed from the portion of the patient and disposed above or in a container (e.g., a vile, a test tube, a petri dish, a culture medium, a test apparatus, a cartridge designed for use with an automated, rapid microbial detection system, or the like) such that at least a portion of the second amount of bodily-fluid can be tested. The withdrawn bodily-fluid can be used for any number of testing processes or procedures such as, for example, blood culture testing, real-time diagnostics, and/or PCR-based approaches. Expanding further, the user can apply a force to the engagement portion 658 of the second member 651 to move the second member 651 in the distal direction. With the first member 641 in its second position (e.g., distal position) and with the elongate portion 613 extending through the first reservoir 680, the bodily-fluid contained within the first reservoir 680 is maintained in fluid isolation with a volume outside the first reservoir 680. Thus, the force applied to the engagement portion 658 moves the second member 651 relative to the first member 641 and the housing 601 in the distal direction to expel a desired portion of the second amount of bodily-fluid from the lumen-defining device and into the container.

Figure 24:
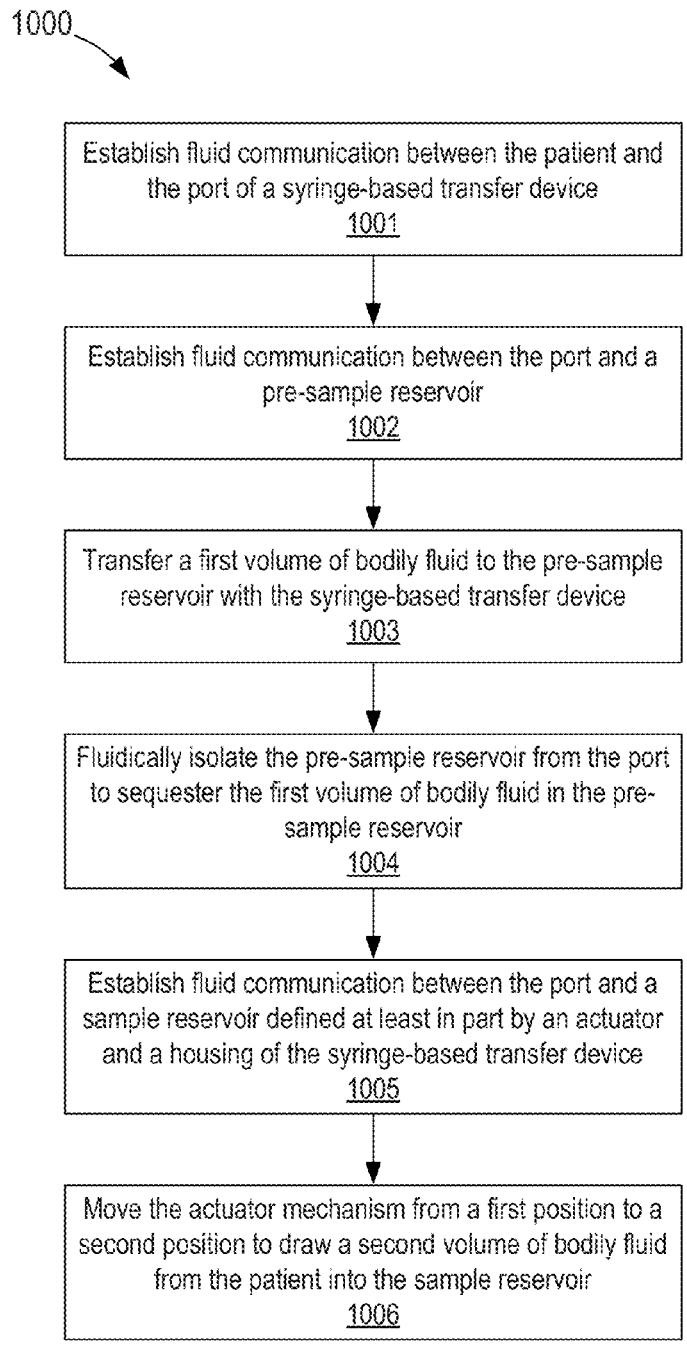
FIG. 24 is a flowchart illustrating a method of using a syringe-based transfer device to obtain a bodily fluid sample from a patient.

FIG. 24 is a flowchart illustrating a method 1000 of using a syringe-based transfer device to obtain a bodily fluid sample from a patient. The syringe-based transfer device can be any suitable device such as those described herein. Accordingly, the syringe-based transfer device can include a housing having a port configured to be coupled to the patient, and an actuator mechanism movably disposed in the housing. For example, the housing, the port, and the actuator mechanism can be substantially similar to or the same as the housing 201, the port 205, and the actuator mechanism 240, respectively, described above with reference to FIGS. 2-6.

The method 1000 includes establishing fluid communication between the patient and the port of the syringe-based transfer device, at 1001. For example, the port can be coupled to a proximal end portion of a lumen-defining device such as, for example, a butterfly needle, a cannula assembly, or the like that is in fluid communication with the patient (e.g., at least a distal end portion of the lumen-defining device is disposed in the body of the patient). With the port physically and fluidically coupled to the lumen-defining device, the port is placed in fluid communication with the body.

With the port coupled to the lumen-defining device, a user can establish fluid communication between the port and a pre-sample reservoir included in and/or defined by the syringe-based transfer device, at 1002. For example, the user can move the actuator mechanism from a first configuration to a second configuration, thereby placing the port in fluid communication with the pre-sample reservoir. In some embodiments, the movement of the actuator mechanism can increase an inner volume which, in turn, can produce a negative pressure within the pre-sample reservoir, as described above with reference to the transfer device 200 in FIG. 5. As described above, in some embodiments, the syringe-based transfer device can be manipulated to modulate the magnitude of suction force by controlling the movement of the actuator mechanism. In this manner, a first volume of bodily-fluid is transferred to the pre-sample reservoir with the syringe-based transfer device, at 1003. In some embodiments, the bodily-fluid can contain undesirable microbes such as, for example, dermally-residing microbes and/or other external contaminants.

The first volume of bodily-fluid can be any suitable volume. For example, in some embodiments, the first volume of bodily-fluid transferred to the pre-sample reservoir can be a predetermined volume. In some embodiments, the first volume can be, for example, about 0.1 ml, about 0.3 ml, about 0.5 ml, about 1.0 ml, about 2.0 ml, about 3.0 ml, about 4.0 ml, about 5.0 ml, about 10.0 ml, about 20 ml, about 50 ml, and/or any volume or fraction of a volume therebetween. In other embodiments, the first volume can be greater than 50 ml or less than 0.1 ml. In some embodiments, the first volume can substantially correspond to the size of the pre-sample reservoir 280. Once the first volume of bodily-fluid is transferred to the pre-sample, reservoir, the pre-sample reservoir is fluidically isolated from the port to sequester the first volume of bodily-fluid in the pre-sample reservoir, at 1004. For example, in some embodiments, the user can move the actuator mechanism and/or otherwise manipulate the syringe-based transfer device to fluidically isolate the pre-sample reservoir.

With the first amount fluidically isolated, fluid communication is established between the port and a sample reservoir defined at least in part by the actuator mechanism and the housing of the syringe-based transfer device, at 1005. For example, in some embodiments, the housing can define an inner volume in which the actuator mechanism is at least partially disposed. In some embodiments, the actuator mechanism can include a seal member or plunger that can form a substantially fluid tight seal with a set of walls defining the inner volume of the housing thereby defining the sample reservoir. For example, the actuator mechanism and the housing can define the sample reservoir in a similar manner as described above with reference to the actuator mechanism 240, the housing 201, and the sample reservoir 290 of FIG. 6. As such, the actuator mechanism can be moved from a first position to a second position to draw a second volume of bodily-fluid from the patient into the sample reservoir, at 1006. With the first volume of bodily-fluid sequestered in the pre-sample reservoir, the second volume of bodily-fluid transferred to the sample reservoir can be substantially free from contaminants such as, for example, dermally residing microbes or the like.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Additionally, certain steps may be partially completed before proceeding to subsequent steps. For example, while the flow control mechanism 430 of the transfer device 400 is described above (with reference to FIG. 15) as being moved prior to the second member 451 of the actuator mechanism 440, in some embodiments, the second member 451 can be moved prior to or concurrently with the flow control mechanism 430.

While various embodiments have been particularly shown and described, various changes in form and details may be made. For example, while the flow control mechanism 430 is shown and described with respect to FIGS. 11-15 as being rotated in a single direction, in other embodiments, a flow control mechanism can be rotated in a first direction (e.g., in the direction of the arrow KK in FIG. 15) and a second direction, opposite the first. In such embodiments, the rotation in the second direction can be configured to move a transfer device through any number of configurations. In other embodiments, the rotation of the flow control mechanism in the second direction can be limited. For example, in some embodiments, the flow control mechanism can be limitedly rotated in the second direction to reduce the diameter of a flow path between the flow control mechanism and a lumen such as to reduce a suction force, as described above.

Although various embodiments have been described as having particular features and/or combinations of components, other embodiments are possible having any combination or sub-combination of any features and/or components from any of the embodiments described herein. For example, while the transfer device 400 is shown in FIGS. 11-15S as not including a valve (e.g., such as those described in the transfer devices 200 and 300), in some embodiments, the transfer device 400 can include a valve. For instance, the transfer device 400 can include a valve in the first lumen 406 of the diverter 409, or at any other suitable position.

The specific configurations of the various components can also be varied. For example, the size and specific shape of the various components can be different than the embodiments shown, while still providing the functions as described herein. More specifically, the size and shape of the various components can be specifically selected for a desired rate of bodily-fluid flow into a fluid reservoir.

The invention claimed is:

1. A syringe-based device for parenterally-procuring bodily fluid samples with reduced contamination from a patient, the device comprising:
   a housing including a proximal end portion and a distal end portion and defining an inner volume therebetween, the proximal end portion being substantially open and the distal end portion having a port configured to be coupled to a lumen-defining device for receiving bodily fluid from the patient;
   a pre-sample reservoir fluidically coupleable to the port and configured to receive and isolate a first volume of bodily fluid withdrawn from the patient; and
   an actuator mechanism at least partially disposed in the inner volume of the housing, the actuator mechanism having a proximal end portion and a distal end portion, the distal end portion including a sealing member and the proximal end portion including a first protrusion and a second protrusion configured to selectively engage with the first protrusion to substantially limit a proximal movement of the second protrusion relative to the first protrusion, and configured to move through the substantially open proximal end portion of the housing when receiving the bodily fluid from the patient into a sample reservoir, the sealing member defining a channel extending from a distal end to a proximal end of the sealing member, the actuator mechanism configured to move between a first configuration in which the bodily fluid can flow from the port to the pre-sample reservoir through the channel in the sealing member, and a second configuration in which the bodily fluid can flow from the port to the sample reservoir, the sample reservoir defined at least in part by the sealing member and the housing.

2. The device of claim 1, wherein the actuator mechanism defines an inner volume between the proximal end portion and the distal end portion of the actuator mechanism.

3. The device of claim 2, wherein the pre-sample reservoir is disposed in the inner volume of the actuator mechanism.

4. The device of claim 2, further comprising:
   a flow control mechanism operable to selectively control fluid flow between the port and the pre-sample reservoir, the flow control mechanism being configured to be moved between a first configuration in which the bodily fluid can flow through a first flow path to the pre-sample reservoir, and a second configuration in which the bodily fluid can flow through a second flow path to the sample reservoir.

5. The device of claim 1, further comprising:
   a valve disposed in the channel.

6. The device of claim 5, wherein the valve is a check valve.

7. The device of claim 1, further comprising:
   a second sealing member having a diameter and disposed within the actuator mechanism, wherein the diameter of the second sealing member is less than a diameter of the sealing member at the distal end portion of the actuator mechanism.

8. A syringe-based device for parenterally-procuring bodily fluid samples with reduced contamination from a patient, the device comprising:
   a housing including a proximal end portion and a distal end portion and defining an inner volume therebetween, the proximal end portion being substantially open and the distal end portion having a port configured to be coupled to a lumen-defining device for receiving bodily fluids from the patient;
   an actuator mechanism movably disposed in the inner volume, the actuator mechanism including a first member having a proximal end portion and a distal end portion and defining an inner volume therebetween, and a second member movably disposed in the inner volume of the first member, the proximal end portion of the first member configured to move through the substantially open proximal end portion of the housing when receiving the bodily fluid samples within the inner volume of the housing,
   the first member including a first plunger disposed at the distal end portion of the first member and a first protrusion disposed at a proximal end portion of the first member, the first plunger including a flow channel configured to allow selective fluid communication between the inner volume defined by the housing and the inner volume defined by the first member, and
   the second member including a second plunger disposed at a distal end portion of the second member and a second protrusion disposed at a proximal end portion of the second member and configured to selectively engage with the first protrusion of the first member to substantially limit a proximal movement of the second member relative to the first member, and configured to move through the substantially open proximal end portion of the housing when receiving the bodily fluid from the patient into a sample reservoir; and mechanical stops configured to prevent removal of the actuator mechanism from the housing.

9. The device of claim 8, further comprising:
a valve disposed in the flow channel.

10. The device of claim 9, wherein the valve is a check valve.

11. The device of claim 8, wherein the actuator mechanism is configured to be moved from a first configuration to a second configuration by application of a first force on the actuator mechanism in a proximal direction, the first plunger, the second plunger, and the first member of the actuator mechanism collectively defining a first fluid reservoir in the second configuration.

12. The device of claim 11, wherein the actuator mechanism is configured to be moved from the second configuration to a third configuration by application of a second force on the actuator mechanism in the proximal direction, the first plunger and the housing defining a second fluid reservoir in the third configuration.

13. The device of claim 12, wherein the first fluid reservoir is fluidically isolated from the second fluid reservoir in the third configuration.

14. The device of claim 12, wherein the first force is substantially the same as the second force.

15. The device of claim 12, wherein the second force is greater than the first force.

16. The device of claim 8, wherein the first plunger has a first diameter and the second plunger has a second diameter, the first diameter being greater than the second diameter.

17. The device of claim 8, wherein the first member and the second member are configured to move independently within the housing.

18. The device of claim 8, wherein the first member and the second member are substantially cylindrical.

19. A device for procuring bodily fluid from a patient, the device comprising:
a housing including a proximal end portion and a distal end portion, the proximal end portion being substantially open and the distal end portion having a port configured to receive the bodily fluid from the patient;
a first member movably disposed within the housing and including a first plunger disposed at a distal end portion of the first member and a first protrusion disposed at a proximal end portion of the first member, the first plunger including a flow channel to allow the body fluid to flow therethrough; and
a second member movably disposed within the first member and including a second plunger disposed at a distal end portion of the second member, the second member including a second protrusion disposed at a proximal end portion of the second member and configured to selectively engage with the first protrusion of the first member to substantially limit a proximal movement of the second member relative to the first member and configured to move through the substantially open proximal end portion of the housing when receiving the bodily fluid from the patient into a sample reservoir.

20. The device of claim 19, further comprising:
a mechanical stop to prevent removal of the first member from the housing.

21. The device of claim 19, further comprising:
a pre-sample reservoir collectively defined by the second plunger, the first plunger, and the first member.

22. The device of claim 21, wherein the second plunger moves away from the first plunger by application of a force by a user on the second member to convey the bodily fluid into the pre-sample reservoir.

23. The device of claim 21, further comprising:
a sample reservoir collectively defined by the first plunger, the distal end portion of the housing, and the housing.

24. The device of claim 23, wherein the first plunger moves away from the port by the second protrusion of the second member engaging with the first protrusion of the first member to convey the bodily fluid into the sample reservoir.

25. The device of claim 23, wherein the sample reservoir is fluidically isolated from the pre-ample reservoir.

26. The device of claim 25, further comprising:
a check valve disposed in the flow channel.

27. The device of claim 19, wherein the flow channel is aligned with the port forming a substantially linear flow path.

28. The device of claim 19, wherein the first plunger has a first diameter and the second plunger has a second diameter, the first diameter being greater than the second diameter.

29. The device of claim 19, wherein the first member and the second member are configured to move independently within the housing.

30. The device of claim 19, wherein the first member and the second member are substantially cylindrical.

* * * * *

UNITED STATES PATENT AND TRADEMARK OFFICE
CERTIFICATE OF CORRECTION

PATENT NO. : 9,999,383 B2
APPLICATION NO. : 14/264481
DATED : June 19, 2018
INVENTOR(S) : Gregory J. Bullington et al.

Page 1 of 1

It is certified that error appears in the above-identified patent and that said Letters Patent is hereby corrected as shown below:

Column 34, Line 33 (Claim 25, Line 2):
"is fluidically isolated from the pre-ample reservoir" should be "is fluidically isolated from the pre-sample reservoir"

Signed and Sealed this
Twenty-eighth Day of August, 2018

Andrei Iancu
*Director of the United States Patent and Trademark Office*